United States Patent
Thornes et al.

(10) Patent No.: US 11,754,541 B2
(45) Date of Patent: Sep. 12, 2023

(54) FLUORINE DETECTION IN A GAS DISCHARGE LIGHT SOURCE

(71) Applicant: Cymer, LLC, San Diego, CA (US)

(72) Inventors: Joshua Jon Thornes, San Diego, CA (US); Rahul Ahlawat, San Diego, CA (US); Edward Siqi Luo, San Diego, CA (US); Gamaralalage G. Padmabandu, San Diego, CA (US)

(73) Assignee: Cymer, LLC, San Diego, CA (US)

( * ) Notice: Subject to any disclaimer, the term of this patent is extended or adjusted under 35 U.S.C. 154(b) by 712 days.

(21) Appl. No.: 16/646,201

(22) PCT Filed: Sep. 10, 2018

(86) PCT No.: PCT/US2018/050301
§ 371 (c)(1),
(2) Date: Mar. 11, 2020

(87) PCT Pub. No.: WO2019/060164
PCT Pub. Date: Mar. 28, 2019

(65) Prior Publication Data
US 2020/0340965 A1    Oct. 29, 2020

Related U.S. Application Data

(60) Provisional application No. 62/562,693, filed on Sep. 25, 2017.

(51) Int. Cl.
*G01N 7/00* (2006.01)
*G01N 33/00* (2006.01)
(Continued)

(52) U.S. Cl.
CPC ..... *G01N 33/0052* (2013.01); *G01N 33/0013* (2013.01); *H01S 3/036* (2013.01); *H01S 3/225* (2013.01)

(58) Field of Classification Search
CPC .......... G01N 33/0052; G01N 33/0013; H01S 3/036; H01S 3/225
See application file for complete search history.

(56) References Cited

U.S. PATENT DOCUMENTS

| 4,412,455 A | 11/1983 | Borgersen |
| 4,535,241 A | 8/1985 | Eberhardt |

(Continued)

FOREIGN PATENT DOCUMENTS

| CN | 1462206 A | 12/2003 |
| CN | 1761615 A | 4/2006 |

(Continued)

OTHER PUBLICATIONS

Bartholomaus et al., "Semiconductor sensors for fluorine detection—optimization for low and high concentrations," Sensors and Actuators B 65, pp. 270-272 (2000).

(Continued)

*Primary Examiner* — Mark Hellner
(74) *Attorney, Agent, or Firm* — DiBerardino McGovern IP Group LLC

(57) ABSTRACT

An apparatus includes: a gas maintenance system having a gas supply system fluidly connected to one or more gas discharge chambers; a detection apparatus fluidly connected to each gas discharge chamber; and a control system connected to the gas maintenance system and the detection apparatus. The detection apparatus includes: a vessel defining a reaction cavity that houses a metal oxide and is fluidly connected to the gas discharge chamber for receiving mixed gas including fluorine from the gas discharge chamber in the reaction cavity, the vessel enabling a reaction between the fluorine of the received mixed gas and the metal oxide to form a new gas mixture including oxygen; and an oxygen sensor fluidly connected to the new gas mixture to sense an amount of oxygen within the new gas mixture. The control (Continued)

system is configured to estimate a concentration of fluorine in the received mixed gas.

12 Claims, 10 Drawing Sheets

(51) Int. Cl.
*H01S 3/036* (2006.01)
*H01S 3/225* (2006.01)

(56) References Cited

U.S. PATENT DOCUMENTS

| | | | |
|---|---|---|---|
| 4,817,413 A | 4/1989 | Asano et al. | |
| 5,017,499 A | 5/1991 | Hakuta et al. | |
| 5,063,035 A | 11/1991 | Leondaridis et al. | |
| 5,149,659 A * | 9/1992 | Hakuta | G01N 33/0052 422/111 |
| 5,978,406 A | 11/1999 | Rokni et al. | |
| 6,240,117 B1 | 5/2001 | Gong et al. | |
| 6,320,892 B1 | 11/2001 | Padmabandu et al. | |
| 6,321,587 B1 | 11/2001 | Laush | |
| 6,514,471 B1 | 2/2003 | Hsiung et al. | |
| 7,835,414 B2 | 11/2010 | Dunstan et al. | |
| 8,411,720 B2 | 4/2013 | O'Brien et al. | |
| 8,767,791 B2 | 7/2014 | Riggs | |
| 10,228,322 B2 | 3/2019 | Duffey | |
| 2002/0051132 A1 | 5/2002 | Ohno et al. | |
| 2003/0185735 A1 | 10/2003 | Hotta et al. | |
| 2004/0191155 A1 | 9/2004 | Mahler et al. | |
| 2005/0117155 A1 | 6/2005 | Kosterev | |
| 2011/0069733 A1 | 3/2011 | Ye et al. | |
| 2011/0214481 A1 | 9/2011 | Kachanov et al. | |
| 2011/0249691 A1 | 10/2011 | O'Brien et al. | |
| 2011/0268639 A1 | 11/2011 | White et al. | |
| 2012/0151994 A1 | 6/2012 | Hung et al. | |
| 2013/0003773 A1 | 1/2013 | O'Brien et al. | |
| 2013/0044314 A1 | 2/2013 | Koulikov et al. | |
| 2013/0136660 A1 | 5/2013 | Utaki et al. | |
| 2013/0239658 A1 | 9/2013 | Lust | |
| 2016/0061784 A1 | 3/2016 | Madhav et al. | |
| 2016/0341602 A1 | 11/2016 | Thornes | |
| 2017/0201057 A1 * | 7/2017 | Ahlawat | H01S 3/2256 |
| 2017/0229832 A1 * | 8/2017 | Ahlawat | H01S 3/2256 |

FOREIGN PATENT DOCUMENTS

| | | | |
|---|---|---|---|
| CN | 1945312 A | 4/2007 | |
| CN | 102043001 A | 5/2011 | |
| CN | 102264455 A | 11/2011 | |
| CN | 102712859 A | 10/2012 | |
| CN | 102834988 A | 12/2012 | |
| CN | 104919312 A | 9/2015 | |
| CN | 105021777 A | 11/2015 | |
| JP | H01308961 A | 12/1989 | |
| JP | H02228086 A | 9/1990 | |
| JP | H0552838 A * | 3/1993 | ............ G01N 31/00 |
| JP | H11274610 A | 10/1999 | |
| JP | 2001-165924 A | 6/2001 | |
| JP | 2001165924 A * | 6/2001 | ............ G01N 31/00 |
| JP | 2002502131 A | 1/2002 | |
| JP | 2010203850 A | 9/2010 | |
| TW | 493069 B | 7/2002 | |
| TW | 201104988 A | 2/2011 | |
| TW | 201246732 A | 11/2012 | |
| TW | 201706579 A | 2/2017 | |
| TW | 201730914 A | 9/2017 | |
| WO | 1999039407 | 8/1999 | |
| WO | 2014143175 A1 | 9/2014 | |

OTHER PUBLICATIONS

Copenheaver, U.S. International Searching Authority, International Search Report and Written Opinion, corresponding PCT Application No. PCT/US2018/050301, dated Nov. 9, 2018, 8 pages total.
Office Action, counterpart Chinese Patent Application No. 201880062088.6, dated Jan. 26, 2022, 22 pages total (including English translation of 11 pages).
Office Action, counterpart Chinese Patent Application No. 201880062088.6, dated Jun. 27, 2022, 23 pages total (including English translation of 11 pages).
Office Action by Mari Otaki of Japan Patent Office, counterpart Japanese Patent Application No. 2020-512802, dated Apr. 20, 2021, 7 pages total (including English translation of 4 pages).
Office Action, Min Young Lee, Examination Bureau of Korean Intellectual Property Office, counterpart Korean Patent Application No. 10-2020-7008692, dated May 27, 2021, 10 pages total (including English translation of 4 pages).
Office Action, Japan Patent Office, counterpart Japanese Patent Application No. 2021-195561, dated Oct. 7, 2022, 9 pages total (including English translation of 5 pages).
Rejection Decision, counterpart Chinese Patent Application No. 201880062088.6, dated Oct. 10, 2022, 23 pages total (including English translation of 15 pages).

* cited by examiner

FLUORINE DETECTION IN A GAS DISCHARGE LIGHT SOURCE

CROSS-REFERENCE TO RELATED APPLICATIONS

This application claims priority of U.S. provisional patent application No. 62/562,693, which was filed on Sep. 25, 2017, and which is incorporated herein in its entirety by reference.

TECHNICAL FIELD

The disclosed subject matter relates to detection of fluorine in a mixed gas.

BACKGROUND

One type of gas discharge light source used in photolithography is known as an excimer light source or laser. An excimer light source typically uses a combination of one or more noble gases, such as argon, krypton, or xenon, and a reactive such as fluorine or chlorine. The excimer light source derives its name from the fact that under the appropriate condition of electrical stimulation (energy supplied) and high pressure (of the gas mixture), a pseudo-molecule called an excimer is created, which only exists in an energized state and gives rise to amplified light in the ultraviolet range.

An excimer light source produces a light beam that has a wavelength in the deep ultraviolet (DUV) range and this light beam is used to pattern semiconductor substrates (or wafers) in a photolithography apparatus. The excimer light source can be built using a single gas discharge chamber or using a plurality of gas discharge chambers.

SUMMARY

In some general aspects, a method includes: receiving at least a portion of a mixed gas from a gas discharge chamber, wherein the mixed gas includes fluorine; reacting the fluorine in the mixed gas portion with a metal oxide to form a new gas mixture including oxygen; sensing a concentration of oxygen within the new gas mixture; and estimating a concentration of fluorine within the mixed gas portion based on the sensed concentration of oxygen.

Implementations can include one or more of the following features. For example, the metal oxide can include aluminum oxide. The metal oxide can lack an alkali metal, an alkaline earth metal, hydrogen, and carbon.

The mixed gas can include an excimer laser gas including at least a mixture of a gain medium and a buffer gas.

The method can also include: adjusting a relative concentration of fluorine in a gas mixture from a set of gas supplies based on the estimated concentration of fluorine in the mixed gas portion; and performing a gas update by adding the adjusted gas mixture to the gas discharge chamber from the gas supplies. The gas update can be performed by filling the gas discharge chamber with a mixture of a gain medium and a buffer gas as well as fluorine. The gas discharge chamber can be filled with the mixture of the gain medium and the buffer gas by filling the gas discharge chamber with a gain medium that includes a noble gas and a halogen, and a buffer gas that includes an inert gas. The noble gas can include argon, krypton, or xenon; the halogen can include fluorine; and the inert gas can include helium or neon. The gas discharge chamber can be filled with the mixture of the gain medium and the buffer gas as well as fluorine by: adding the mixture of the gain medium and the buffer gas as well as fluorine to an existing mixed gas in the gas discharge chamber; or replacing an existing mixed gas in the gas discharge chamber with at least the mixture of the gain medium and the buffer gas as well as fluorine. The gas update can be performed by performing one or more of a gas refill scheme or a gas injection scheme.

The method can also include determining whether the concentration of fluorine in the new gas mixture falls below a lower value. The concentration of oxygen within the new gas mixture can be sensed by sensing the concentration of oxygen within the new gas mixture only if it is determined that the concentration of fluorine in the new gas mixture has fallen below the lower value. The lower value can be a value determined based on one or more of a damage threshold and an error threshold of a sensor that senses the concentration of oxygen within the new gas mixture. The lower value can be 0.1 parts per million. The method can include interacting the new gas mixture with an oxygen sensor to sense the concentration of oxygen only if it is determined that the concentration of fluorine in the new gas mixture has fallen below the lower value.

The portion of the mixed gas can be received from the gas discharge chamber before a gas update is to be performed on the gas discharge chamber. The gas update can include adding a gas mixture to the gas discharge chamber from a set of gas supplies, wherein the gas mixture includes at least some fluorine. The gas update can be performed by performing one or more of a gas refill scheme or a gas injection scheme.

The portion of the mixed gas can be received from the gas discharge chamber by bleeding the mixed gas from the gas discharge chamber and directing the bled mixed gas to a reaction vessel that houses the metal oxide. The method can include transferring the new gas mixture from the reaction vessel to a measurement vessel. The concentration of oxygen within the new gas mixture can be sensed by sensing the concentration of oxygen within the new gas mixture within the measurement vessel. The concentration of oxygen within the new gas mixture can be sensed by exposing a sensor within the measurement vessel to the new gas mixture.

The method can include, after the concentration of fluorine within the mixed gas portion has been estimated, exhausting the new gas mixture from the measurement vessel.

The concentration of oxygen within the new gas mixture can be sensed by sensing the concentration of oxygen within the new gas mixture without diluting the mixed gas portion with another material.

The mixed gas portion can be reacted with the metal oxide to form the new gas mixture including oxygen by forming an inorganic fluoride compound plus oxygen. The metal oxide can include aluminum oxide, and the inorganic fluoride compound can include aluminum fluoride. The total pore volume of the aluminum oxide can be at least 0.35 cubic centimeters per gram.

The concentration of oxygen within the new gas mixture can be sensed by sensing the concentration of oxygen within the new gas mixture only after a pre-determined period of time has elapsed after the beginning of the reaction.

The mixed gas portion can be an exhaust gas and reacting the mixed gas portion with the metal oxide to form the new gas mixture including oxygen can include removing fluorine from the exhaust gas.

The concentration of fluorine within the mixed gas portion can be estimated based on the sensed concentration of oxygen by estimating based only on the sensed concentration of oxygen and the chemical reaction between fluorine in the mixed gas portion and the metal oxide.

The concentration of fluorine in the mixed gas portion can be about 500-2000 parts per million.

The reaction of the fluorine in the mixed gas portion with the metal oxide to form the new gas mixture including oxygen can be a stable reaction. The fluorine in the mixed gas portion can be reacted with the metal oxide to form the new gas mixture including oxygen by performing a reaction that is linear and provides a direct correlation between the concentration of fluorine in the mixed gas portion and the concentration of the oxygen in the new gas mixture.

In other general aspects, a method includes: performing a first gas update by adding a first gas mixture from a set of gas supplies to a gas discharge chamber; removing at least a portion of a mixed gas from the gas discharge chamber after the first gas update, wherein the mixed gas includes fluorine; reacting the fluorine of the removed mixed gas portion with a reactant to form a new gas mixture including oxygen; sensing a concentration of oxygen within the new gas mixture; estimating a concentration of fluorine within the removed mixed gas portion based on the sensed concentration of oxygen; adjusting a relative concentration of fluorine in a second gas mixture from the set of gas supplies based on the estimated concentration of fluorine in the removed mixed gas portion; and performing a second gas update by adding the adjusted second gas mixture to the gas discharge chamber from the gas supplies.

Implementations can include one or more of the following features. For example, the method can include: determining whether the concentration of fluorine in the new gas mixture falls below a lower value that is based on one or more of a damage threshold and an error threshold of a sensor that senses the concentration of oxygen within the new gas mixture. The concentration of oxygen within the new gas mixture can be sensed by sensing the concentration of oxygen within the new gas mixture only if it is determined that the concentration of fluorine in the new gas mixture has fallen below the lower value.

The reactant can include metal oxide. The mixed gas in the gas discharge chamber can include an excimer laser gas including at least a mixture of a gain medium and a buffer gas.

The concentration of fluorine within the removed mixed gas portion can be estimated based on the sensed concentration of oxygen by estimating the fluorine concentration within the removed mixed gas portion without measuring the fluorine concentration within the removed mixed gas portion.

In other general aspects, an apparatus includes a gas maintenance system including a gas supply system fluidly connected to one or more gas discharge chambers of an excimer gas discharge system; a detection apparatus fluidly connected to each gas discharge chamber of the excimer gas discharge system; and a control system connected to the gas maintenance system and the detection apparatus. The detection apparatus includes: a vessel defining a reaction cavity that houses a metal oxide and is fluidly connected to the gas discharge chamber for receiving mixed gas including fluorine from the gas discharge chamber in the reaction cavity, the vessel enabling a reaction between the fluorine of the received mixed gas and the metal oxide to form a new gas mixture including oxygen; and an oxygen sensor configured to be fluidly connected to the new gas mixture and, when fluidly connected to the new gas mixture, sense an amount of oxygen within the new gas mixture. The control system is configured to: receive the output of the oxygen sensor and estimate a concentration of fluorine in the mixed gas received from the gas discharge chamber; determine whether a concentration of fluorine in a gas mixture from the gas supply system of the gas maintenance system should be adjusted based on the estimated concentration of fluorine in the mixed gas; and send a signal to the gas maintenance system to adjust the relative concentration of fluorine in a gas mixture supplied from the gas supply system of the gas maintenance system to the gas discharge chamber during a gas update to the gas discharge chamber.

Implementations can include one or more of the following features. For example, each gas discharge chamber of the excimer gas discharge system can house an energy source and can contain a gas mixture that includes an excimer laser gas including a gain medium and fluorine.

The detection apparatus can also include a fluorine sensor fluidly connected to the reaction cavity and configured to determine whether a concentration of fluorine in the new gas mixture falls below a lower value, the lower value being a value determined based on one or more of a damage threshold and an error threshold of the oxygen sensor. The control system can be connected to the fluorine sensor. The control system can be configured to: receive the determination from the fluorine sensor that the fluorine concentration in the new gas mixture falls below the lower value; and only permit the oxygen sensor to interact with the new gas mixture if it is determined that the concentration of fluorine in the new gas mixture falls below the lower value.

The detection apparatus can include a measurement vessel fluidly connected to the reaction cavity of the reaction vessel and defining a measurement cavity that is configured to receive the new gas mixture. The oxygen sensor can be configured to sense an amount of oxygen within the new gas mixture in the measurement cavity.

The oxygen sensor can be configured to operate within an acceptable range only if the concentration of fluorine in the new gas mixture falls below a lower value.

The concentration of fluorine in the removed mixed gas portion can be about 500-2000 parts per million.

The excimer gas discharge system can include a plurality of gas discharge chambers, and the detection apparatus can be fluidly connected to each gas discharge chamber of the plurality. The detection apparatus can include a plurality of vessels, each vessel defining a reaction cavity that houses the metal oxide, and each vessel being fluidly connected to one of the gas discharge chambers and the detection apparatus can include a plurality of oxygen sensors, each oxygen sensor associated with one vessel.

The excimer gas discharge system can include a plurality of gas discharge chambers, and the detection apparatus can be fluidly connected to each gas discharge chamber of the plurality. The detection apparatus can include a plurality of vessels, each vessel defining a reaction cavity that houses the metal oxide, and each vessel being fluidly connected to one of the gas discharge chambers and the detection apparatus can include a single oxygen sensor that is fluidly connected with all of the vessels.

DESCRIPTION

Figure 1:
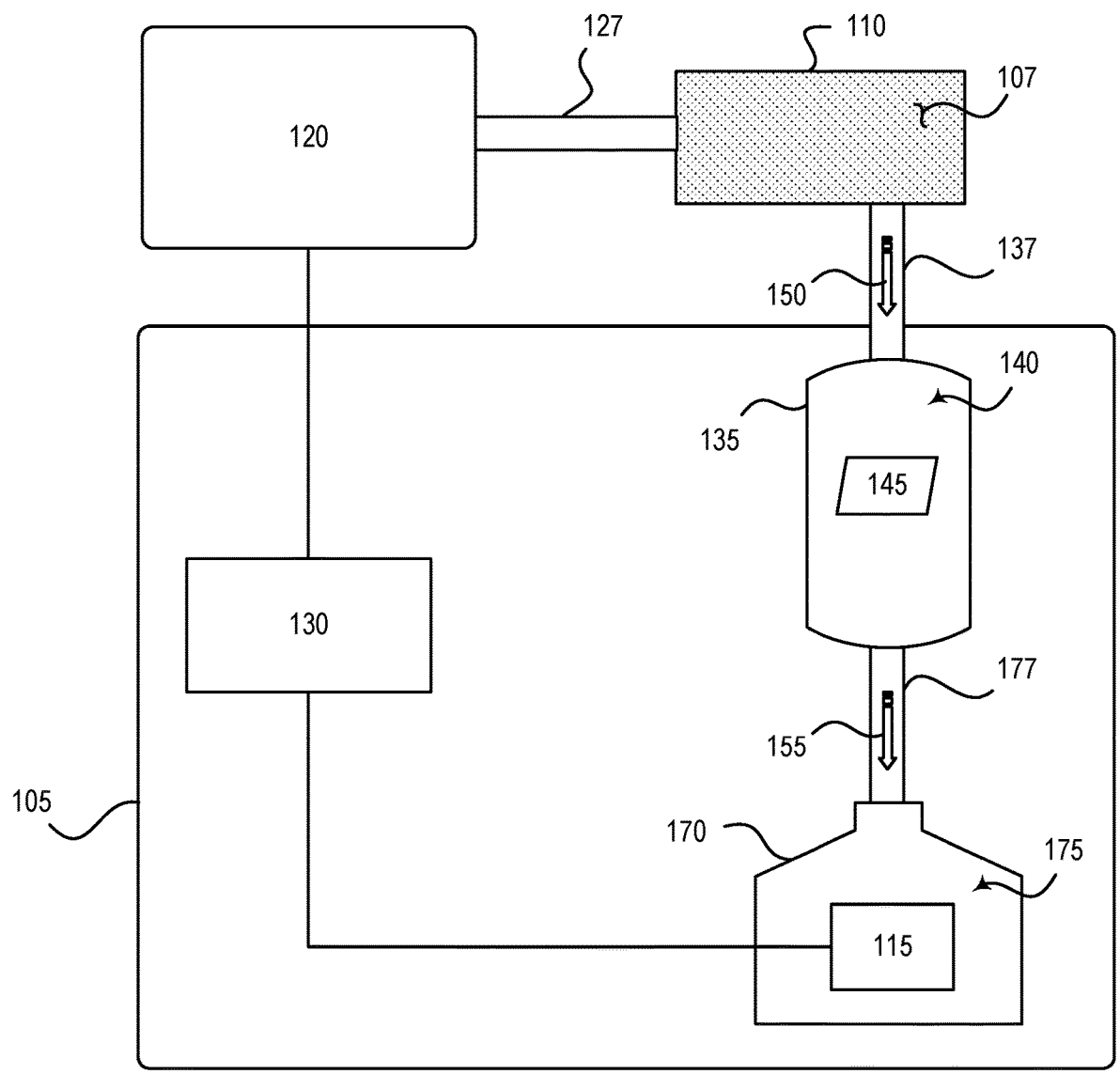
FIG. 1 is a block diagram of an apparatus including a detection apparatus configured to measure a concentration of fluorine in a gas mixture within a chamber.

Referring to FIG. 1, an apparatus 100 includes a detection apparatus 105 that is configured to measure or estimate a concentration of fluorine (F) in a gas mixture 107 within a chamber 110 without directly measuring the concentration of fluorine in the gas mixture 107 using a commercially-available fluorine sensor. At room temperature, fluorine is a gas of diatomic molecules and is represented by its molecular structure $F_2$. The term "fluorine" as used herein therefore refers to molecular fluorine $F_2$. The concentration of fluorine molecules $F_2$ in the chamber 110 is in a range that is too high to permit a direct detection of the fluorine. For example, the concentration of fluorine in the chamber 110 is greater than about 500 parts per million (ppm) and can be around 1000 ppm or up to about 2000 ppm. However, commercially-available fluorine sensors typically saturate at 10 ppm, thus making it unrealistic to use a commercially-available fluorine sensor to directly measure the concentration of fluorine in the chamber 110. Instead, the detection apparatus 105 enables a chemical reaction that converts the fluorine from the chamber 110 into a gas (such as oxygen) that can be detected and measured with a commercially-available sensor 115. The detection apparatus 105 can calculate how much fluorine was present before the beginning of the chemical reaction based on the amount of oxygen present after the chemical reaction (as supplied from the sensor 115) and based on information about the chemical reaction.

In order for this estimation to be accurate, the detection apparatus 105 can assume that the chemical reaction that converts the fluorine from the chamber 110 into the oxygen gas is a linear reaction in which there is a direct correlation between the concentration of the fluorine before the beginning of the chemical reaction and the concentration of the oxygen at the end of the chemical reaction. Or, the detection apparatus 105 can assume that the conversion of the fluorine is complete (and thus, there exists no residual molecular fluorine $F_2$ in the gas after the chemical reaction).

The apparatus 100 includes a gas maintenance system 120 that includes at least a gas supply system fluidly connected to the chamber 110 via a conduit system 127. As discussed in detail below, the gas maintenance system 120 includes one or more supplies of gases and a control unit (that also includes a valve system) for controlling which of the gases from the supplies are transferred into or out of the chamber 110 via the conduit system 127.

The detection apparatus 105 includes a controller 130 that receives the output from the oxygen sensor 115 and calculates how much fluorine was present before the beginning of the chemical reaction to estimate the amount of fluorine in the gas mixture 107. The controller 130 uses this information to determine whether a concentration of fluorine in the gas mixture 107 needs to be adjusted. The controller 130 therefore determines how to adjust the relative amounts of gases in the supplies of the gas maintenance system 120 that are to be transferred into or out of the chamber 110 based on the determination. The controller 130 sends a signal to the gas maintenance system 120 to adjust the relative concentration of fluorine in the gas mixture 107 during a gas update to the chamber 110.

The detection apparatus 105 includes a reaction vessel 135 that defines a reaction cavity 140 that houses a metal oxide 145. The reaction cavity 140 is fluidly connected to the chamber 110 via a conduit 137 to receive a mixed gas 150 including the fluorine from the chamber 110. Although not shown, one or more fluid control devices (such as valves) can be placed in the conduit 137 to control the timing of when the mixed gas 150 is directed to the reaction cavity 140 as well as to control a rate of flow of the mixed gas 150 into the reaction vessel 135. In this way, the reaction cavity 140 enables the chemical reaction between the fluorine of the received mixed gas 150 and the metal oxide 145 to form a new gas mixture 155. The interior of the reaction vessel 135 that defines the reaction cavity 140 should be made of a non-reactive material so as not to interfere with or alter the chemical reaction between the fluorine of the received mixed gas 150 and the metal oxide 145. For example, the interior of the reaction vessel 135 can be made of a non-reactive metal such as stainless steel or Monel metal.

The oxygen sensor 115 is fluidly connected to receive the new gas mixture 155 and to sense an amount of oxygen within the new gas mixture 155. The oxygen sensor 115 can be a commercially available oxygen sensor that is able to detect a concentration of oxygen in a range of concentrations that are expected due to the chemical reaction. For example, the oxygen sensor 115 senses oxygen within the new gas mixture 155 in a range of 200-1000 ppm.

One example of an oxygen sensor that is suitable for this range of concentrations is an oxygen analyzer that utilize a precision zirconia oxide sensor for the detection of oxygen. The zirconia oxide sensor includes a cell made of a high purity, high density, stabilized zirconia ceramic. The zirconia oxide sensor produces a voltage signal indicative of the oxygen concentration of the new gas mixture 155. Moreover, the output of the zirconia oxide sensor is analyzed (for example, converted and linearized) by a high-speed microprocessor within the oxygen sensor 115 to provide a direct digital readout for use by the controller 130. A conventional zirconium oxide cell includes a zirconium oxide ceramic tube plated with porous platinum electrodes on its inner and outer surfaces. As the sensor is heated above a specific temperature (for example, 600 C or 1112° F.), it becomes an oxygen ion-conducting electrolyte. The electrodes provide a catalytic surface for the change in oxygen molecules, $O_2$, to oxygen ions, and oxygen ions to oxygen molecules. Oxygen molecules on the high concentration reference gas side of the cell gain electrons to become ions which enter the electrolyte. Simultaneously, at the inner electrode, oxygen ions lose electrons and become released from the surface as oxygen molecules. When the oxygen concentration differs on each side of the sensor, oxygen ions migrate from the high concentration side to the low concentration side. This ion flow creates an electronic imbalance resulting in a DC voltage across the electrodes. This voltage is a function of the sensor temperature and the ratio of oxygen partial pressures (concentrations) on each side of the sensor. This voltage is then analyzed by the high-speed microprocessor within the oxygen sensor 115 for direct readout by the controller 130.

The oxygen sensor 115 can be inside a measurement cavity 175 of a measurement vessel 170. The measurement cavity 175 is fluidly connected to the reaction cavity 140 via a conduit 177. Although not shown in FIG. 1, one or more fluid control devices (such as valves) can be placed in the conduit 177 to control the timing of when the new gas mixture 155 is directed to the measurement cavity 175 as well as to control a rate of flow of the new gas mixture 155 into the measurement vessel 170.

The fluorine in the mixed gas 150 is reacted with metal oxide 145 because the chemical reaction between the fluorine and metal oxide is a stoichiometrically simple chemical reaction that is easy to implement and control. Moreover, the controlled stoichiometric ratio of the chemical reaction is fixed. Additionally, the chemical reaction between the fluorine and the metal oxide is a stable chemical reaction. A chemical reaction can be stable if the chemical reaction is not reversing and the components of the new gas mixture do not react with anything else in the new gas mixture to form fluorine. One suitable chemical reaction between the fluorine of the mixed gas 150 and the metal oxide 145 that is stable and has a controlled stoichiometric ratio is discussed next.

In some implementations, the metal oxide 145 is in a powder form. Moreover, the metal oxide 145 in powder form can be closely packed into the reaction vessel 135 (which can be a tube) so that there is no movement of the particles in the powder of the metal oxide 145. The area or volume in the space outside the powder of the metal oxide 145 and within the reaction vessel 135 is considered as pores and by using the metal oxide 145 in a powder form, it is possible to ensure that there is a large surface area to allow a thorough chemical reaction between the metal oxide 145 and the fluorine. In some implementations, and depending on the specific metal oxide, the metal oxide 145 and the reaction vessel 135 are maintained at room temperature and the reaction between the metal oxide 145 and the fluorine proceeds without the need for a catalyst.

The metal oxide 145 includes a metal such as aluminum. Moreover, the metal oxide 145 lacks an alkali metal, an alkaline earth metal, hydrogen, and carbon. Thus, the metal oxide 145 can be alumina (which is aluminum oxide or $Al_2O_3$). The alumina is in a powder and solid form and is typically an orange color powder with enough pores to provide for enough surface area to allow the chemical reaction with the fluorine gas. The space between the particles of the powder is large enough to permit the flow of fluorine gas into the alumina to enable the chemical reaction.

For example, the alumina can be in the form of a powder or grains that are packed in a column and have a total pore volume of at least 0.35 cubic centimeters per gram. The mixed gas 150 is passed (for example, flowed) through or across the metal oxide 145 to enable the chemical reaction between the fluorine and the alumina.

In the presence of the fluorine gas ($F_2$) within the mixed gas 150, the following chemical reaction occurs:

$$6F_2 + 2Al_2O_3 = 4AlF_3 + 3O_2.$$

For every six molecules of fluorine ($F_2$) that interact with two molecules of the metal oxide ($Al_2O_3$) 145, four molecules of an inorganic fluoride compound (aluminum fluoride or $AlF_3$) and three molecules of oxygen ($O_2$) are output. This chemical reaction is a linear and stoichiometrically simple reaction. Thus, to just focus on the fluorine and the oxygen, for every two molecules of fluorine $F_2$ input into the chemical reaction, one molecule of oxygen $O_2$ is output from the chemical reaction. Thus, if the concentration of fluorine $F_2$ that is input into the chemical reaction is 1000 ppm, then a concentration of 500 ppm of oxygen $O_2$ is released after the chemical reaction and is detected by the sensor 115. Thus, for example, because the detection apparatus 105 knows that the ratio of fluorine to oxygen is 2:1 in this chemical reaction, if 600 ppm of oxygen is detected by the sensor 115, then that means that 1200 ppm of fluorine was present in the gas mixture 107. In other implementations, the detection apparatus 105 can assume that the conversion of the fluorine is complete (and thus, there exists no residual molecular fluorine $F_2$ in the gas after the chemical reaction). For example, this assumption can be a valid assumption if enough time has passed after the beginning of the chemical reaction.

In some implementations, the reaction between the metal oxide 145 and the fluorine in the mixed gas 150 happens under one or more specifically designed conditions. For example, the reaction between the metal oxide 145 and the fluorine in the mixed gas 150 can happen under the presence of one or more catalysts, which are substances that change the rate of the chemical reaction, but are chemically unchanged at the end of the chemical reaction. As another example, the reaction between the metal oxide 145 and the fluorine in the mixed gas 150 can happen in a controlled environment such as a temperature-controlled environment or a humidity-controlled environment.

Figure 2:
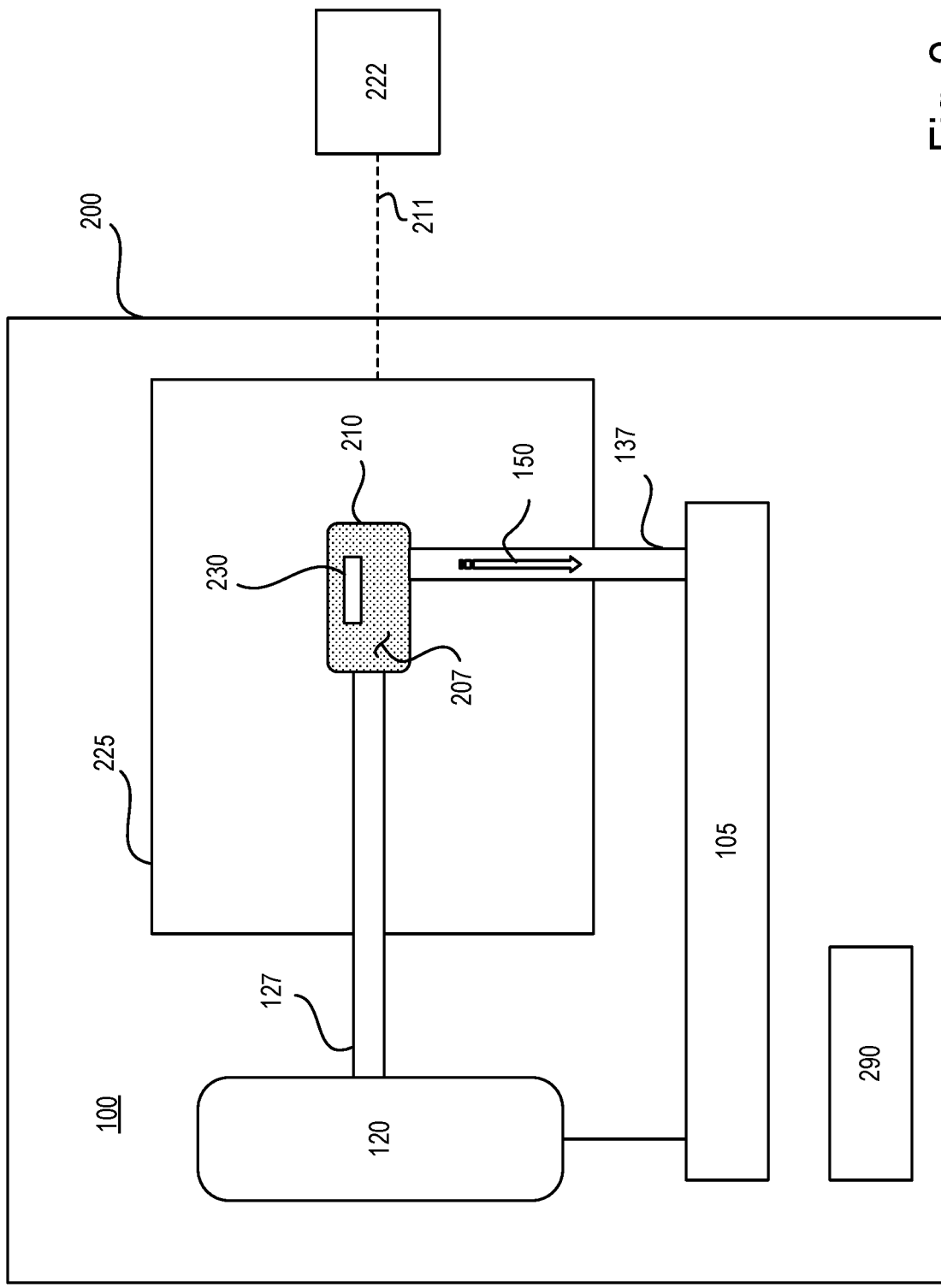
FIG. 2 is a block diagram of the apparatus of FIG. 1 implemented as a part of a deep ultraviolet (DUV) light source that produces a light beam directed to a photolithography apparatus.

Referring to FIG. 2, the apparatus 100 can be, for example, within a deep ultraviolet (DUV) light source 200 that produces a light beam 211 that is directed to a photolithography apparatus 222 for patterning microelectronic features on a wafer. The DUV light source 200 includes a control system 290 connected to various elements of the DUV light source 200 to enable production of the light beam 211. While the control system 290 is shown as a monolithic block, it can be made up of a plurality of sub-components, any one or more of the sub-components can be remove from other sub-components or local to elements within the DUV light source 200. Moreover, the controller 130 can be considered as a part of the control system 290.

In this implementation, the detection apparatus 105 is configured to calculate the concentration of fluorine within one or more of the gas discharge chambers 210 of an excimer gas discharge system 225 that produces the light beam 211 of the DUV light source 200. While only one gas discharge chamber 210 is shown, the excimer gas discharge system 225 can include a plurality of gas discharge chambers 210, any one or more of them being in fluid communication with the detection apparatus 105, as well as other elements (such as optical elements, metrology devices, and electromechanical elements) for controlling aspects of the light beam 211, such other elements not shown in FIG. 2. Moreover, only the components of the DUV light source 200 related to the detection apparatus 105 are shown in FIG. 2. For example, the DUV light source 200 can include a beam preparation system placed at the output of the last gas discharge chamber 210 to adjust one or more properties of the light beam 211 directed to the photolithography apparatus 222.

The gas discharge chamber 210 houses an energy source 230 and contains the gas mixture 207. The energy source 230 provides a source of energy to the gas mixture 207; specifically, the energy source 230 provides enough energy to the gas mixture 207 to cause a population inversion to enable gain via stimulated emission within the chamber 210. In some examples, the energy source 230 is an electric discharge provided by a pair of electrodes placed within the gas discharge chamber 210. In other examples, the energy source 230 is an optical pumping source.

The gas mixture 207 includes a gain medium that includes a noble gas and a halogen such as fluorine. During operation of the DUV light source 200, the fluorine of the gas mixture 207 (which provides the gain medium for light amplification) within the gas discharge chamber 210 is consumed and over time this reduces the amount of light amplification and thus changes characteristics of the light beam 211 produced by the light source 200. The photolithography apparatus 222 seeks to maintain a concentration of fluorine within the gas mixture 207 in the gas discharge chamber 210 to within a certain tolerance compared to a concentration of the fluorine that is set at an initial gas refill procedure. Because of this, additional fluorine is added to the gas discharge chamber 210 on a regular cadence and under the control of the gas maintenance system 120. The amount of fluorine consumption varies from gas discharge chamber to gas discharge chamber, so closed loop control is used to determine the amount of fluorine to push or inject into the gas discharge chamber 210 at each opportunity. The detection apparatus 105 is used to determine the concentration of fluorine remaining in the gas discharge chamber 210, and thus is used in an overall scheme to determine the amount of fluorine to push or inject into the gas discharge chamber 210.

As mentioned, the gas mixture 207 includes the gain medium that includes the noble gas and the fluorine. The gas mixture 207 can include other gases, such as a buffer gas. The gain medium is the laser-active entity within the gas mixture 207, and the gain medium can be composed of single atoms, molecules or pseudo-molecules. Thus, a population inversion occurs in the gain medium via stimulated emission by pumping the gas mixture 207 (and therefore the gain medium) with an electric discharge from the energy source 230. As mentioned above, the gain medium typically includes a noble gas and a halogen, while the buffer gas typically includes an inert gas. The noble gas includes, for example, argon, krypton, or xenon. The halogen includes, for example, fluorine. The inert gas includes, for example, helium or neon. The gases other than fluorine within the gas mixture 207 are inert (rare gases or noble gases) and because of this, it is assumed that the only chemical reaction that takes place between the mixed gas 150 and the metal oxide 145 is the reaction between the fluorine of the mixed gas 150 and the metal oxide 145.

Referring again to FIG. 1, the gas maintenance system 120 is a gas management system for adjusting characteristics (such as relative concentrations or pressures of components within the gas mixture 107 or 207).

Figure 3:
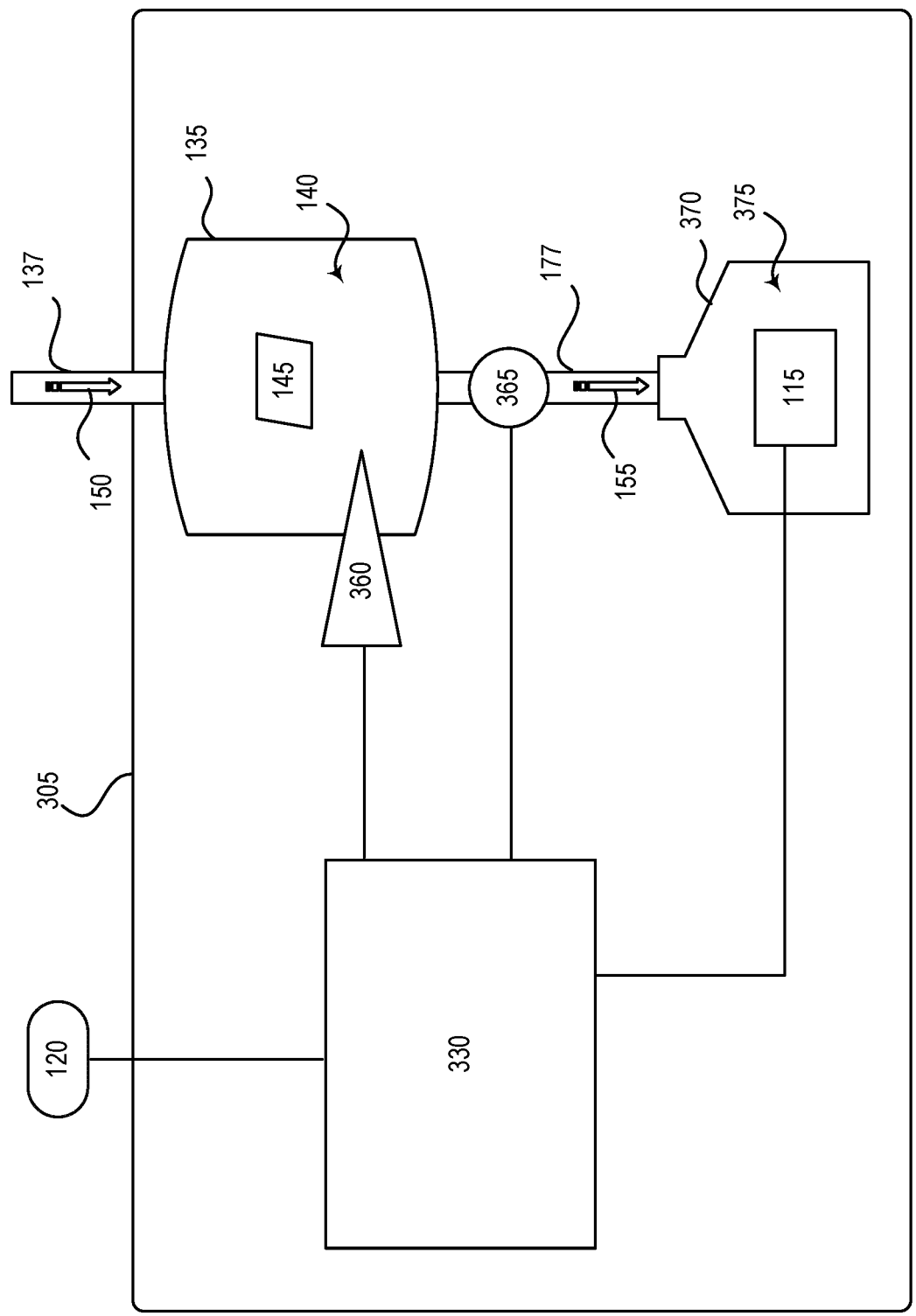
FIG. 3 is a block diagram of an implementation of the detection apparatus of the apparatus of FIG. 1, in which the detection apparatus includes a fluorine sensor.

Referring to FIG. 3, in some implementations, the detection apparatus 105 is a detection apparatus 305 that includes a fluorine sensor 360 fluidly connected to the reaction cavity 140 and configured to determine when a concentration of fluorine in the new gas mixture 155 falls below a lower value. The fluorine sensor 360 can be a commercially-available fluorine sensor that saturates above a concentration of fluorine that is too low to use for a direct measurement of fluorine in the mixed gas 150. However, the fluorine sensor 360 has a minimum detection threshold and can be used to thereby detect when the concentration of the fluorine in the new gas mixture 155 falls below the lower value. For example, the fluorine sensor 360 could saturate at a concentration of 10 ppm but it could have a minimum detection threshold of about 0.05 ppm and can start to detect the fluorine in the new gas mixture 155 after the concentration of the fluorine in the new gas mixture 155 falls below 0.1 ppm.

The controller 130 is configured as a controller 330 that receives the output from the fluorine sensor 360. The controller 330 includes a module that interacts with a flow control device 365 in the line that transports the new gas mixture 155 to the oxygen sensor 115. The flow control device 365 can be a device such as a gate valve or other fluid-control valve.

The controller 330 sends a signal to the flow control device 365 to enable the flow of the new gas mixture 155 to the oxygen sensor 115 only if it determines from the output of the fluorine sensor 360 that the concentration of the fluorine in the new gas mixture 155 falls below the lower value (for example, 0.1 ppm). In this way, the oxygen sensor 115 is only exposed to the new gas mixture 155 if the concentration of fluorine falls below the lower value, thereby protecting the oxygen sensor 115 from unacceptable levels of fluorine. The lower value can be a value determined based on a damage threshold of the oxygen sensor 115. Thus, at concentrations of fluorine above the lower value, damage can be caused to the oxygen sensor 115. The lower value can be a value determined based on an error threshold of the oxygen sensor 115. Thus, at concentrations of fluorine above the lower value, measurement errors can impact the accuracy of the oxygen sensor 115.

The detection apparatus 305 also includes a measurement vessel 370 fluidly connected to the reaction cavity 140 of the reaction vessel 135. The measurement vessel 370 defines a measurement cavity 375 that is configured to receive the new gas mixture 155. Moreover, the oxygen sensor 115 is housed within the measurement cavity 375. The measurement vessel 370 is any vessel that contains the new gas mixture 155 to enable the oxygen sensor 115 to sense the concentration of oxygen in the new gas mixture 155. The interior of the measurement vessel 370 that defines the measurement cavity 375 should be made of a non-reactive material so as not to change the composition of the new gas mixture 155. For example, the interior of the measurement vessel 370 can be made of a non-reactive metal.

Figure 4:
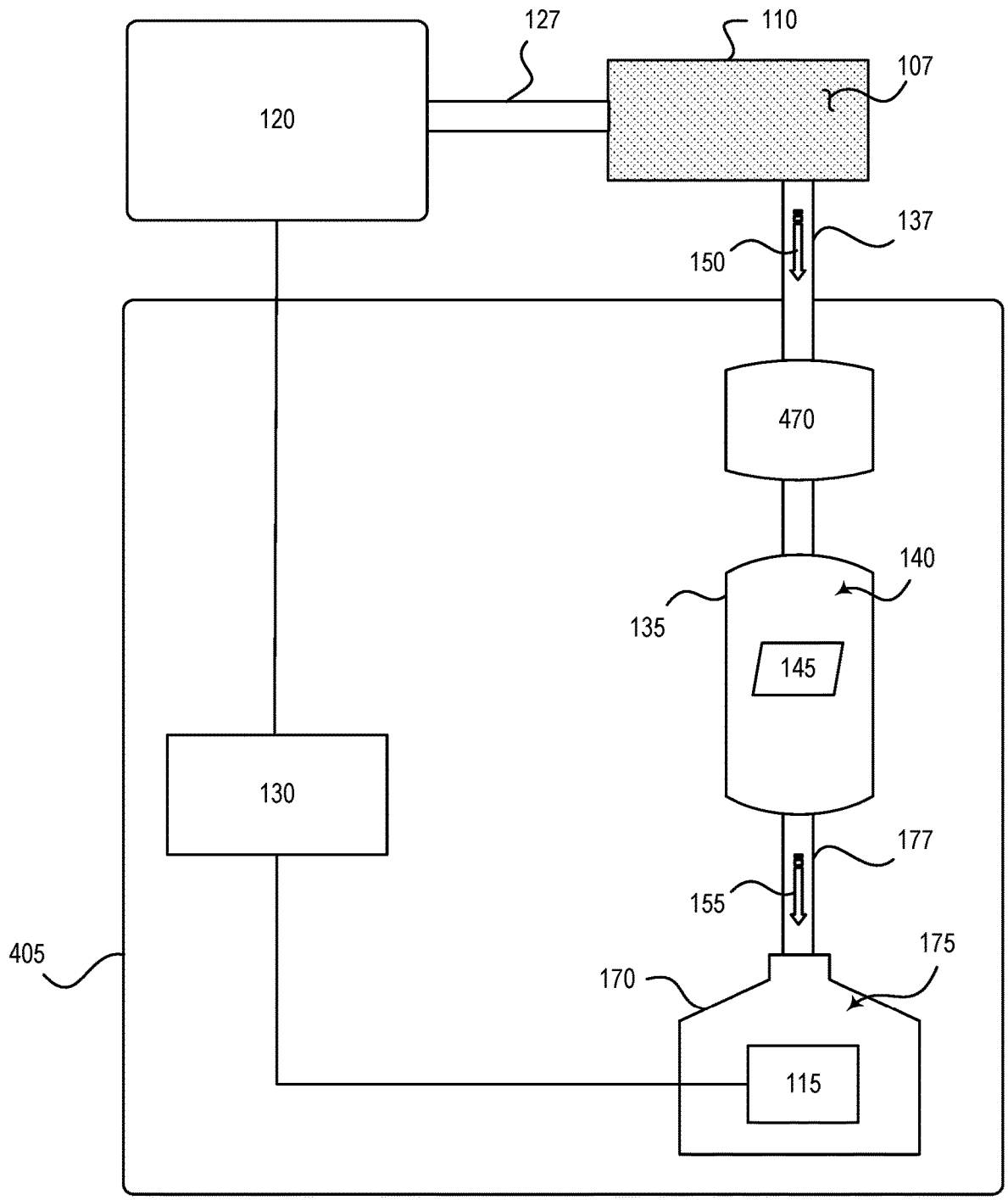
FIG. 4 is a block diagram of an implementation of the apparatus of FIG. 1, in which the detection apparatus includes a buffer vessel.

Referring to FIG. 4, in some implementations, the detection apparatus 105 is designed as a detection apparatus 405 that includes a buffer vessel 470 that decouples the flow rate of the exhaust from the chamber 110 from a flow rate required for the reaction vessel 135. In this way, the buffer vessel 470 enables the fluorine measurement via the detection apparatus 105 without affecting the steady-state operation of the gas exchange performed by the gas maintenance system 120.

In one example, the concentration of fluorine within the chamber 110 is about 1000 ppm, the volume of the chamber 110 is 36 liters (L), and the pressure within the chamber 110 is 200-400 kilopascals (kPa). The interior cavity of the buffer vessel 470 has a volume of about 0.1 L and a pressure of 200-400 kPa. The measurement cavity 175 has a volume of 0.1 L, a pressure of about 200-400 kPa, and a concentration of oxygen of about 500 ppm. After the sensor 115 performs the measurement of the oxygen concentration, and outputs the data to the controller 130, then the measurement cavity 175 can be emptied in a controlled manner.

Figure 5:
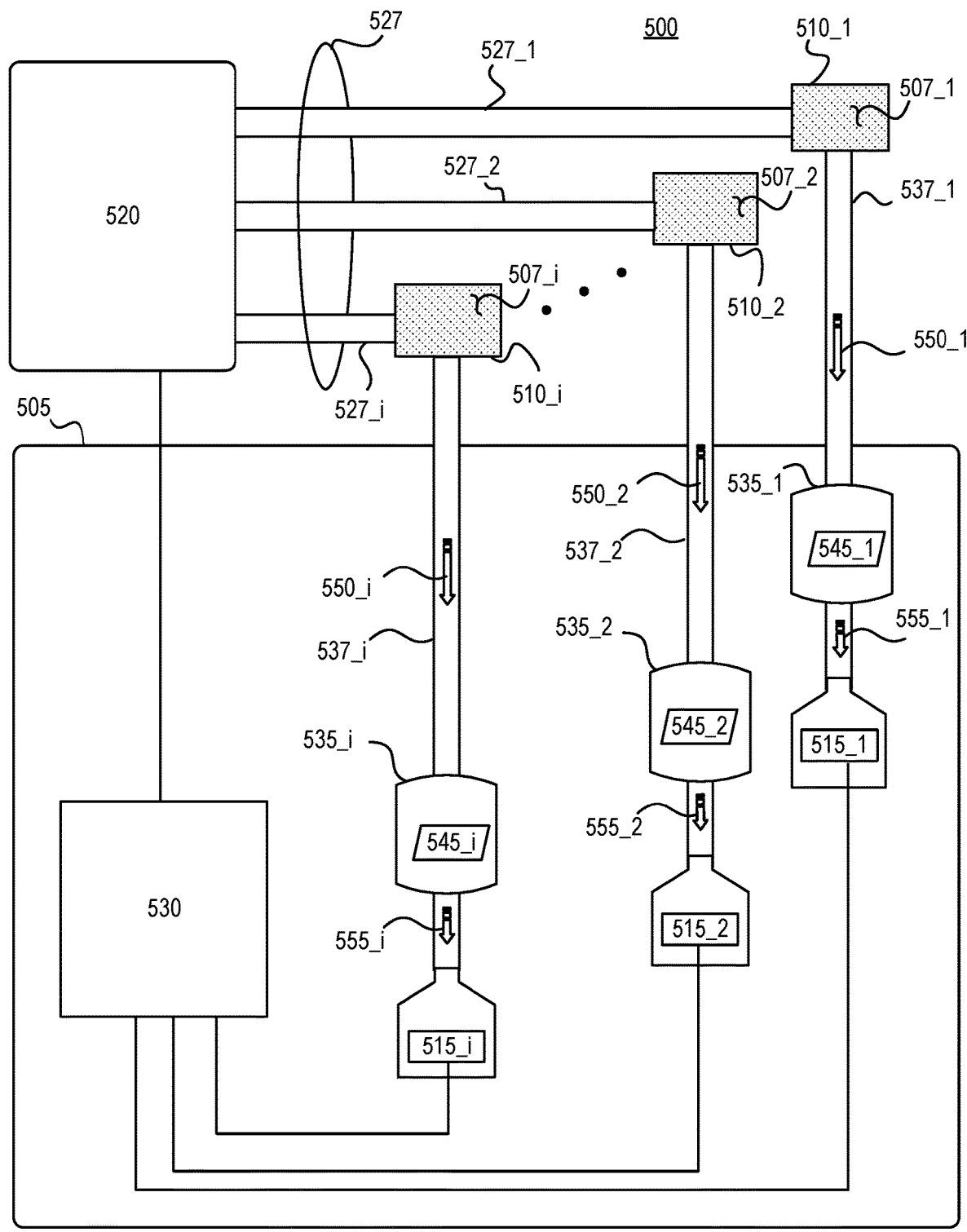
FIG. 5 is a block diagram of an implementation of the apparatus of FIG. 1, in which the detection apparatus includes a plurality of reaction vessels, each reaction vessel associated with one of a plurality of chambers.

As mentioned above with reference to FIG. 1, the detection apparatus 105 is configured to measure or estimate the concentration of fluorine in the gas mixture 107 in the chamber 110. In some implementations, as shown in FIG. 5, the detection apparatus 105 is designed as a detection apparatus 505 that is configured to measure or estimate the concentration of fluorine in the gas mixture 507_1, 507_2, . . . 507_$i$ in a respective chamber 510_1, 510_2, . . . 510_$i$, where i is an integer number greater than 1 as a part of an apparatus 500. In the detection apparatus 505, there is a separate or dedicated oxygen sensor 515_1, 515_2, . . . 515_$i$ associated with a respective chamber 510_1, 510_2, . . . 510_$i$. In this way, each sensor 515_1, 515_2, . . . 515_$i$ can be used to measure the fluorine concentration in the respective chamber 510_1, 510_2, . . . 510_$i$.

The detection apparatus 505 is connected to the gas maintenance system 520, which includes the gas supply system that is fluidly connected to each chamber 510_1, 510_2, . . . 510_$i$ via the respective conduit system 527_1, 527_3, . . . 527_$i$ that is a part of a master conduit system 527. The gas maintenance system 520 includes one or more supplies of gases and a control unit for controlling which of the gases from the supplies are transferred into and out of the respective chamber 510_1, 510_2, . . . 510_$i$ view the master conduit system 527. The detection apparatus 505 includes a respective reaction vessel 535_1, 535_2, . . . 535_$i$ that receives the mixed gas 550_1, 550_2, . . . 550_$i$ (which includes the fluorine) from the respective chamber 510_1, 510_2, . . . 510_$i$ via respective conduits 537_1, 537_2, . . . 537_$i$. The new gas mixture 555_1, 555_2, . . . 555_$i$ formed by the chemical reaction between fluorine of the received mixed gas 550_1, 550_2, . . . 550_$i$ and the metal oxide 545_1, 545_2, . . . 545_$i$ in the respective reaction vessel 535_1, 535_2, . . . 535_$i$ is then directed to the respective oxygen sensor 515_1, 515_2, . . . 515_$i$.

The detection apparatus 505 also includes a controller 530 that is connected to the gas maintenance system 520 and to each of the oxygen sensors 515_1, 515_2, . . . 515_$i$. Like the controller 530, the controller 530 receives the outputs from the oxygen sensors 515_1, 515_2, . . . 515_$i$ and calculates how much fluorine was present before the beginning of the chemical reaction in the reaction vessel 535_1, 535_2, . . . 535_$i$ to estimate the amount of fluorine in the respective gas mixture 507_1, 507_2, . . . 507_$i$.

In other implementations, it is possible to use a single sensor 515 that measures the fluorine in all of the chambers 510_1, 510_2, . . . 510_$i$, as long as the detection apparatus 505 includes suitable plumbing between the chambers 510_1, 510_2, . . . 510_$i$ and the detection apparatus 505 to prevent cross-talk between the measurements performed by the sensor 515 for each of the chambers 510_1, 510_2, . . . 510_$i$. Moreover, a single sensor 515 design can work if a gas exchange is only performed on one chamber 510 at a time and thus the controller 530 can measure the fluorine in a single chamber 510 at any one moment.

Figure 6:
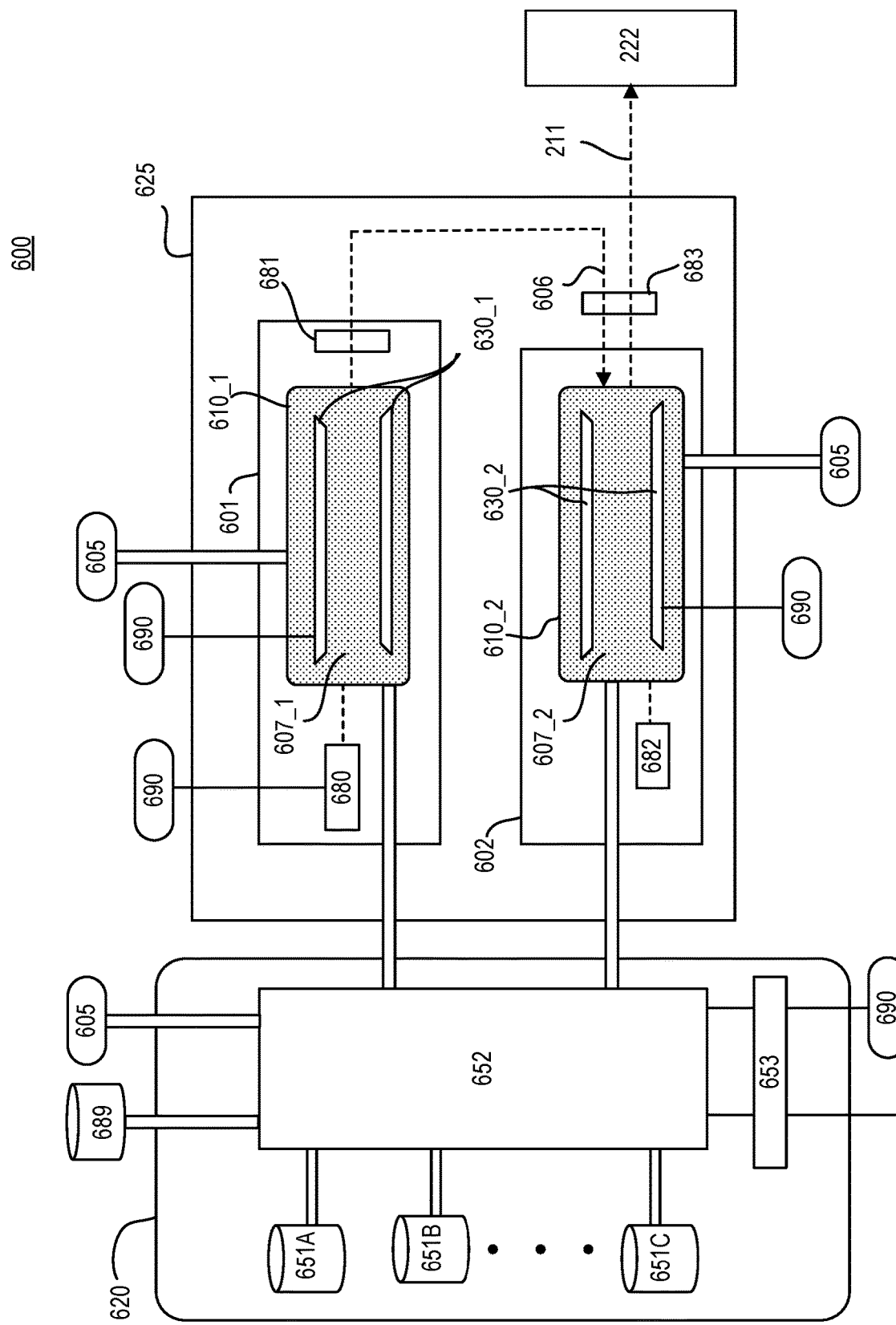
FIG. 6 is a block diagram of an implementation of the apparatus of FIG. 2, in which details of an exemplary DUV light source are shown.

Referring to FIG. 6, an exemplary DUV light source 600 is shown that incorporates a detection apparatus 605 such as the detection apparatus 105 of FIG. 1, 3, 4, or 5. The DUV light source 600 includes an excimer gas discharge system 625 that is a dual-stage pulsed output design. The gas discharge system 625 has two stages: a first stage 601 that is a master oscillator (MO) that outputs a pulsed amplified light beam 606 and a second stage 602 that is a power amplifier (PA) that receives the light beam 606 from the first stage 601. The first stage 601 includes a MO gas discharge chamber 610_1 and the second stage 602 includes a PA gas discharge chamber 610_2. The MO gas discharge chamber 610_1 includes as its energy source two elongated electrodes 630_1. The electrodes 630_1 provide a source of energy to a gas mixture 607_1 within the chamber 610_1. The PA gas discharge chamber 610_2 includes as its energy source two elongated electrodes 630_2, which provide a source of energy to a gas mixture 607_2 within the chamber 610_2.

The MO 601 provides the light beam 606 (which can be referred to as a seed light beam) to the PA 602. The MO gas discharge chamber 610_1 houses the gas mixture 607_1 that includes a gain medium in which amplification occurs and the MO 601 also includes an optical feedback mechanism such as an optical resonator that is formed between a spectral feature selection system 680 on one side of the MO gas discharge chamber 610_1 and an output coupler 681 on a second side of the MO gas discharge chamber 610_1.

The PA gas discharge chamber 610_2 houses the gas mixture 607_2 that includes a gain medium 607_2 in which amplification occurs when seeded with the seed light beam 606 from the MO 601. If the PA 602 is designed as a regenerative ring resonator, then it is described as a power ring amplifier (PRA), and in this case, enough optical feedback can be provided from the ring design. The PA 602 includes a beam return 682 that returns (via reflection, for example), the light beam back into the PA gas discharge chamber 610_2 to form a circulating and closed loop path in which the input into the ring amplifier intersects the output out of the ring amplifier at a beam coupling apparatus 683.

The MO 601 enables fine tuning of spectral parameters such as the center wavelength and the bandwidth at relatively low output pulse energies (when compared with the output of the PA 602). The PA receives the seed light beam 606 from the MO 601 and amplifies this output to attain the necessary powers for the output light beam 211 to use in the output apparatus such as the photolithography apparatus 222. The seed light beam 606 is amplified by repeatedly passing through the PA 602 and the spectral features of the seed light beam 606 are determined by the configuration of the MO 601.

The gas mixture 607_1, 607_2 used in the respective gas discharge chamber 610_1, 610_2 can be a combination of suitable gases for producing an amplified light beam (such as the seed light beam 606 and the output light beam 211) around the required wavelengths and bandwidth. For example, the gas mixture 607_1, 607_2 can include argon fluoride (ArF), which emits light at a wavelength of about 193 nanometers (nm), or krypton fluoride (KrF), which emits light at a wavelength of about 248 nm.

The detection apparatus 605 includes a gas maintenance system 620 that is a gas management system for the excimer gas discharge system 625, and specifically for the gas discharge chambers 610_1 and 610_2. The gas maintenance system 620 includes one or more gas sources 651A, 651B, 651C, etc. (such as sealed gas bottles or canisters) and a valve system 652. The one or more gas sources 651A, 651B, 651C, etc. are connected to the MO gas discharge chamber 610_1 and the PA gas discharge chamber 610_2 through a set of valves within the valve system 652. In this way, gas can be injected into the respective gas discharge chamber

610_1 or 610_2 with specific relative amounts of components within the gas mixture. Although not shown, the gas maintenance system 620 can also include one or more other components such as flow restrictors, exhaust valves, pressure sensors, gauges, and test ports.

Each of the gas discharge chambers 610_1 and 610_2 contains a mixture of gases (the gas mixture 607_1, 607_2). As an example, the gas mixture 607_1, 607_2 contains a halogen, such as fluorine, along with other gases such as argon, neon, and possibly others in different partial pressures that add up to a total pressure. For example, if the gain medium used in the gas discharge chamber 610_1, 610_2 is argon fluoride (ArF), then the gas source 651A contains a mixture of gases including halogen fluorine, the noble gas argon, and one or more other rare gases such as buffer gases (which can be an inert gas such as neon). This sort of mixture within the gas source 651A can be referred to as a tri-mix since it contains three kinds of gases. In this example, another gas source 651B can contain a mixture of gases including argon and one or more other gases but none of the fluorine. This sort of mixture in the gas source 651B can be referred to as a bi-mix since it contains two kinds of gases.

The gas maintenance system 620 can include a valve controller 653 that is configured to send one or more signals to the valve system 652 to cause the valve system 652 to transfer gases from specific gas sources 651A, 651B, 651C, etc. into the gas discharge chambers 610_1, 610_2 in a gas update. A gas update can be a refill of the gas mixture 607 within the gas discharge chamber in which an existing mixed gas in the gas discharge chamber is replaced with at least a mixture of the gain medium and a buffer gas as well as fluorine. A gas update can be an inject scheme in which a mixture of the gain medium and the buffer gas as well as the fluorine are added to an existing mixed gas in the gas discharge chamber.

Figure 7:
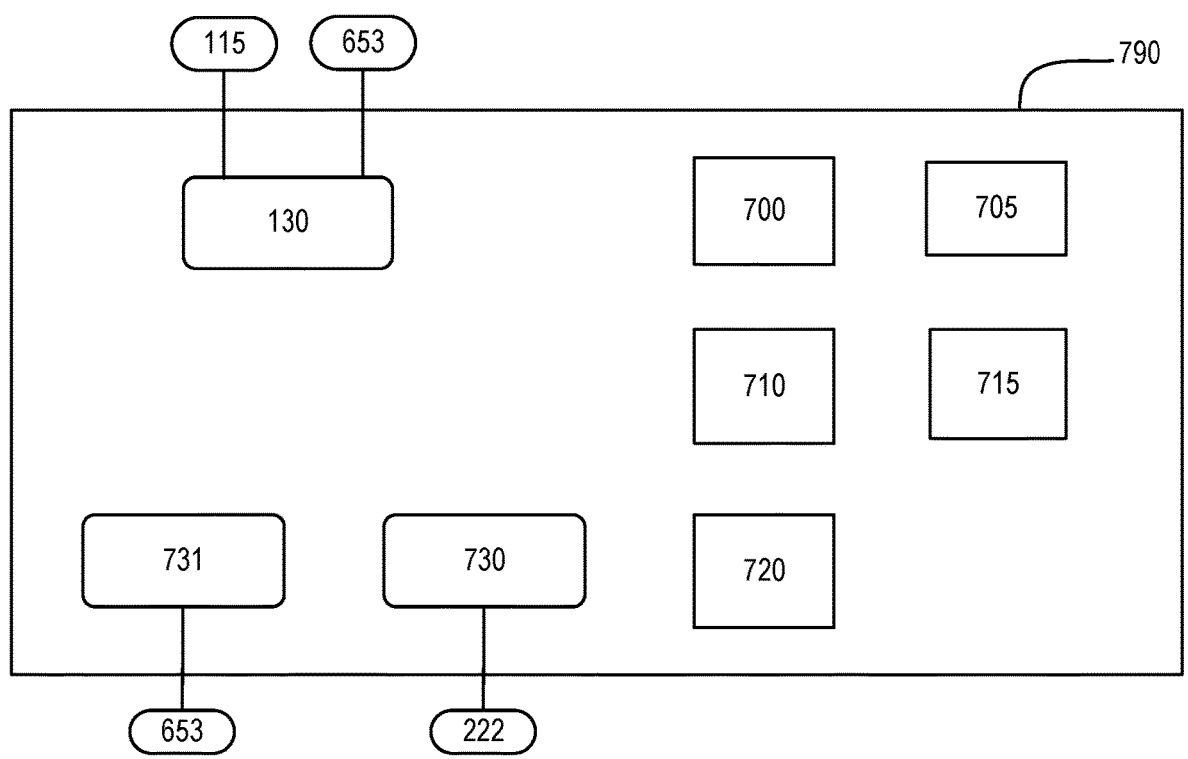
FIG. 7 is a block diagram of an implementation of a control system that is a part of the DUV light source shown in FIG. 2 or 6.

Alternatively, or additionally, the valve controller 653 can send one or more signals to the valve system 652 to cause the valve system 652 to bleed gas from the discharge chambers 610_1, 610_2 when necessary, and such bled gas can be vented to a gas dump represented as 689. In some implementations, it is possible that the bled gas is instead fed to the detection apparatus 605, as shown in FIG. 7.

During operating of the DUV light source 600, the fluorine of the argon (or krypton) fluoride molecule (which provides the gain medium for light amplification) within the gas discharge chambers 610_1, 610_2 is consumed and over time this reduces the amount of light amplification and therefore the energy of the light beam 211 that is used by the photolithography apparatus 222 for wafer processing. Moreover, during operation of the DUV light source 600, contaminants can enter the gas discharge chambers 610_1, 610_2. Accordingly, it is necessary to inject gases from one or more of the gas sources 651A, 651B, 651C, etc. into the gas discharge chambers 610_1, 610_2 in order to flush contaminants out or to replenish the fluorine that is lost.

A plurality of gas sources 651A, 651B, 651C, etc. are needed because the fluorine in the gas source 651A is at a particular partial pressure that is typically higher than that desired for laser operation. In order to add fluorine to a gas chamber 610_1 or 610_2 at a desired lower partial pressure, the gas in the gas source 651A can be diluted, and the non-halogen containing gas in the gas source 651B can be used for this purpose.

Although not shown, the valves of the valve system 652 can include a plurality of valves assigned to each of the gas discharge chambers 610_1 and 610_2. For example, an injection valve can be used that allows gas to pass into and out of each gas discharge chamber 610_1, 610_2 at a first flow rate. As another example, a chamber fill valve can be used that allows gas to pass into and out of each gas discharge chamber 610_1, 610_2 at a second flow rate that is distinct from (for example, faster than) the first flow rate.

When a refill scheme is performed on a gas discharge chamber 610_1 or 610_2, all of the gas in the gas discharge chamber 610_1 or 610_2 is replaced by, for example, emptying the gas discharge chamber 610_1 or 610_2 (by bleeding the gas mixture out to the gas dump 689) and then refilling that gas discharge chamber 610_1 or 610_2 with a fresh gas mixture. The refill is performed with the goal of obtaining a specific pressure and concentration of fluorine in the gas discharge chamber 610_1 or 610_2. When an injection scheme is performed on a gas discharge chamber 610_1 or 610_2, the gas discharge chamber is not emptied or is only bled a small amount before a gas mixture is injected into the gas discharge chamber. In both sorts of gas updates, the detection apparatus 605 (which is designed similarly to the detection apparatus 105) can receive some of the bled gas mixture as the mixed gas 150 for analysis within the detection apparatus 605 to determine the concentration of the fluorine within the gas discharge chamber 610_1 or 610_2 so as to determine how to perform the gas update.

The valve controller 653 interfaces with the detection apparatus 605 (and specifically the controller 130 in the detection apparatus 605). Additionally, the valve controller 653 can interface with other control modules and subcomponents that are a part of a control system 690, which is discussed next.

Referring to FIG. 7, a control system 790 (which can be the control system 290 or 690) that is a part of the DUV light source (such as the light source 200 or 600) is shown in block diagram. Details about the control system 790 are provided that relate to the aspects of the detection apparatus 105/605 and the method relating to gas control and fluorine concentration estimation described herein. Moreover, the control system 790 can include other features not shown in FIG. 7. In general, the control system 790 includes one or more of digital electronic circuitry, computer hardware, firmware, and software.

The control system 790 includes memory 700, which can be read-only memory and/or random access memory. Storage devices suitable for tangibly embodying computer program instructions and data include all forms of non-volatile memory, including, by way of example, semiconductor memory devices, such as EPROM, EEPROM, and flash memory devices;

magnetic disks such as internal hard disks and removable disks; magneto-optical disks; and CD-ROM disks. The control system 790 can also include one or more input devices 705 (such as a keyboard, touch screen, microphone, mouse, hand-held input device, etc.) and one or more output devices 710 (such as a speaker or a monitor).

The control system 790 includes one or more programmable processors 715, and one or more computer program products 720 tangibly embodied in a machine-readable storage device for execution by a programmable processor (such as the processors 715). The one or more programmable processors 715 can each execute a program of instructions to perform desired functions by operating on input data and generating appropriate output. Generally, the processor 715 receives instructions and data from memory 700. Any of the foregoing may be supplemented by, or incorporated in, specially designed ASICs (application-specific integrated circuits).

The control system 790 can also include, among other components or modules, the controller 130, 330, 530 (represented as box 130 in FIG. 7) of the detection apparatus 105 and the a gas maintenance module 731 that interfaces with the valve controller 653 of the gas maintenance system 620. Each of these modules can be a set of computer program products executed by one or more processors such as the processors 715. Moreover, any of the controllers/modules 130, 731 can access data stored within the memory 700.

Connections between controllers/features/modules within the control system 790 and between controllers/features/modules within the control system 790 and other components of the apparatus 100 (which can be the DUV light source 600) can be wired or wireless.

While only a few modules are shown in FIG. 7, it is possible for the control system 790 to include other modules. Additionally, although the control system 790 is represented as a box in which all of the components appear to be co-located, it is possible for the control system 790 to be made up of components that are physically remote from each other in space or time. For example, the controller 130 can be physically co-located with the sensor 115 or the gas maintenance system 120. As another example, the gas maintenance module 731 can be physically co-located with the valve controller 653 of the gas maintenance system 620 and can be separate from the other components of the control system 790.

Additionally, the control system 790 can include a lithography module 730 that receives instructions from the lithography controller of the photolithography apparatus 222 for example, with instructions to measure or estimate a concentration of fluorine within the gas mixture 107 of the chamber 110.

Figure 8:
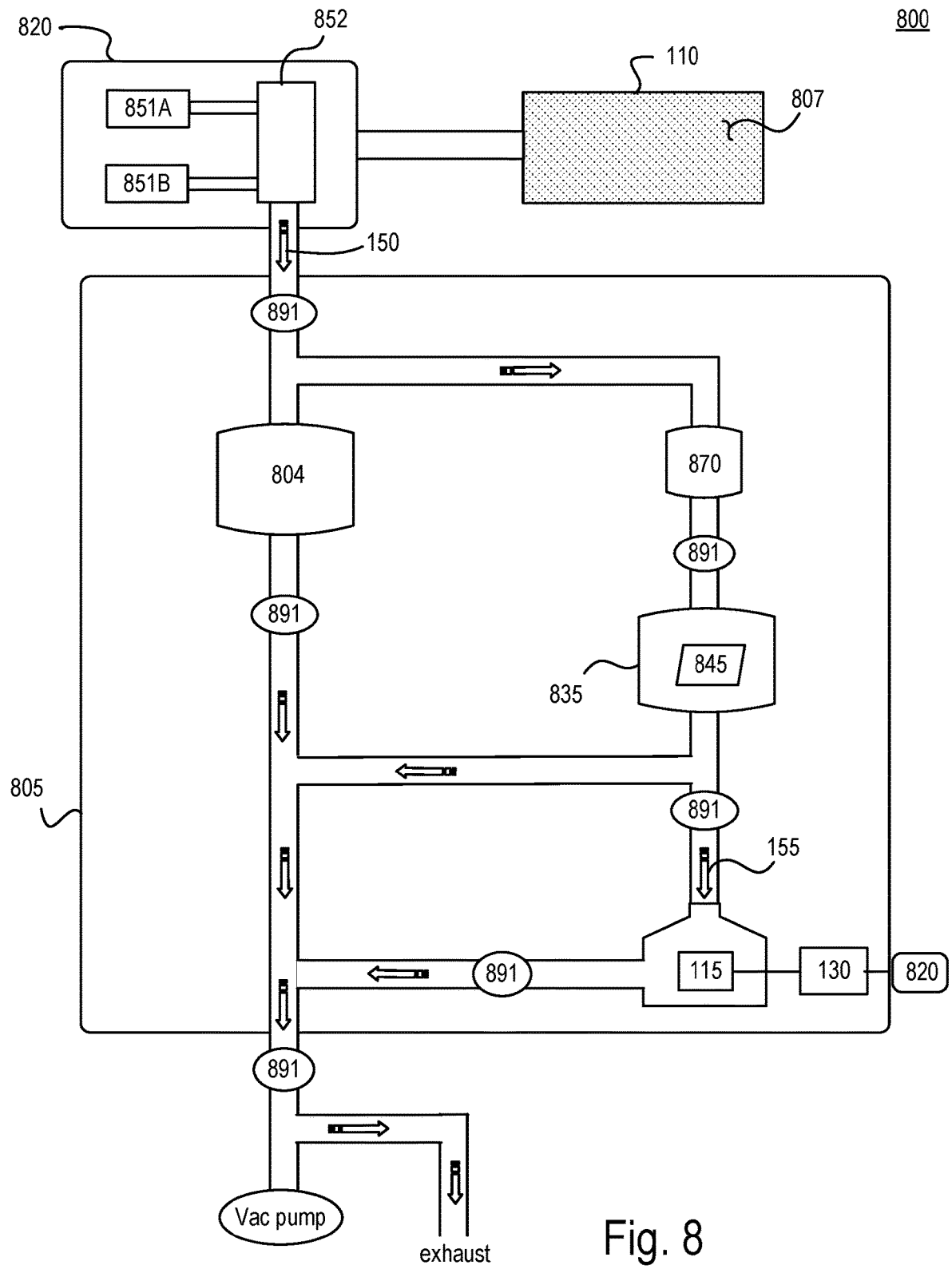
FIG. 8 is a block diagram of another implementation of the apparatus of FIG. 1, in which the apparatus is implemented in conjunction with a fluorine scrubber.

Referring to FIG. 8, in some implementations, the detection apparatus 105 is designed as a detection apparatus 805 that works in parallel with a fluorine scrubber 804 that is in fluid communication with a gas maintenance system 820. The fluorine scrubber 804 is used in conjunction with the gas maintenance system 820 to properly exhaust the gas mixture 807 from the chamber 110 by chemically reacting the fluorine within the gas mixture 807 to form chemicals that can be safely disposed of, for example, via an exhaust.

A portion of the mixed gas 150 that is bled out of the gas maintenance system 820 is directed to the buffer vessel 870 and then to another fluorine scrubber 835 that includes the metal oxide 845. The fluorine in the mixed gas 150 chemically reacts with the metal oxide 845 in the fluorine scrubber 835 (in the manner discussed above) and is converted to a new gas mixture 155 that includes the oxygen. The new gas mixture 155 is directed to the oxygen sensor 115, where it is sensed. The controller 130 estimates the concentration of oxygen as well as the concentration of fluorine within the mixed gas 150 and the gas mixture 107 and determines how to adjust the gas maintenance system 820 to perform a gas update. In this example, the gas maintenance system 820 includes a valve system 852 fluidly connected to a source of tri-mix 851A and a source of bi-mix 851B. Various control valves 891 are placed along the lines to control the flow rates and to control the amount of gas that is directed through the lines.

Figure 9:
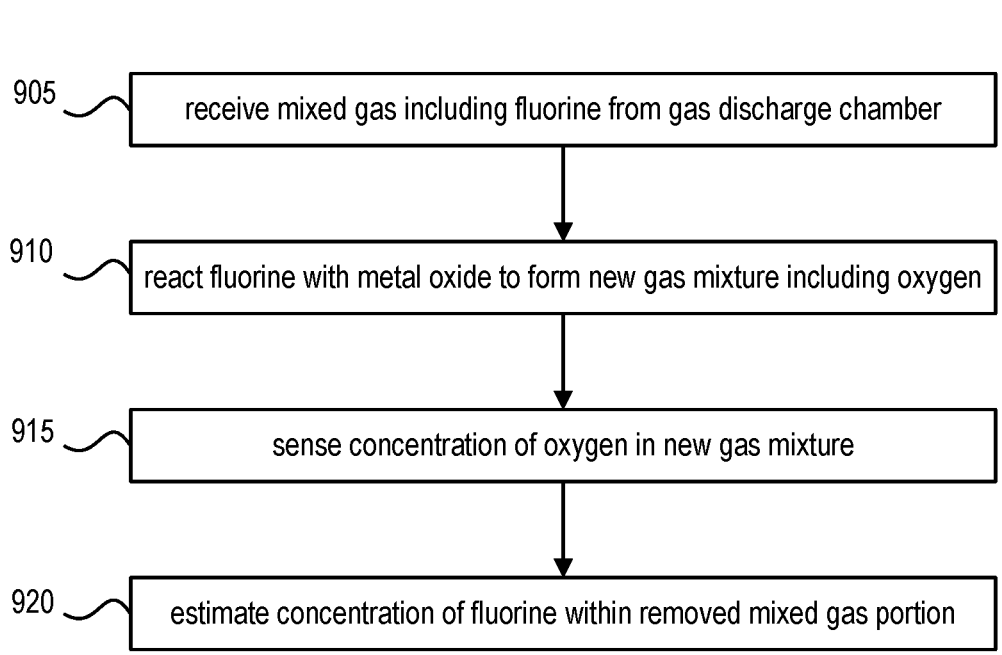
FIG. 9 is a flow chart of a procedure performed by the detection apparatus for detecting a concentration of fluorine in the gas mixture of the chamber.

Referring to FIG. 9, a procedure 900 is performed by the detection apparatus 105 for detection of a concentration of fluorine in the gas mixture 107 of the chamber 110. Reference is made to the apparatus of FIG. 1 but the procedure 900 applies to the detection apparatuses described with reference to FIGS. 2-8 as well. The detection apparatus 105 receives a portion of the mixed gas 150 including fluorine from the gas discharge chamber 110 (905). The fluorine in the mixed gas 150 is chemically reacted with the metal oxide 145 to form the new gas mixture 155, which includes oxygen (910). The concentration of oxygen in the new gas mixture 155 is sensed, for example, with the sensor 115 (915). And, the concentration of fluorine in the mixed gas 150 is estimated based on the sensed concentration of oxygen (920).

The detection apparatus 105 can receive the mixed gas 150 (905) by bleeding (releasing under pressure) the gas mixture 107 from the chamber 110. For example, the gas maintenance system 120 can include a collection of valves that enable the gas mixture 107 to be bled from the chamber 110 and then directed as the mixed gas 150 to the detection apparatus 105. The pressure in the chamber 110 can be used to pressurize the reaction vessel 135 or the buffer vessel 470, for example, by using a series of valves and a vacuum pump to create a negative pressure, the gas mixture 107 is pushed out of the chamber 110 and to the detection apparatus 105. The amount of mixed gas 150 that is needed in the reaction vessel 135 can be determined based on the need of the oxygen sensor 115 to get a precise and stable reading. A limiting factor on the amount of mixed gas 150 is the fluorine conversion capacity of the metal oxide 145 in the reaction cavity 140. For example, it is desirable to have a precise reading from the oxygen sensor 115, but also it is desirable to minimize total gas flow, so that the metal oxide 145 can have a maximum lifetime of use.

The mixed gas 150 that is received (905) by the detection apparatus 105 can be a mixed gas 150 that is exhausted from the chamber 110 toward a fluorine scrubber, and therefore the mixed gas 150 can be considered as an exhaust gas. Such an implementation is shown in FIG. 8, in which the fluorine in the mixed gas 150 chemically reacts with the metal oxide 845 in the fluorine scrubber 835 and is converted to the new gas mixture 155 that includes the oxygen.

The procedure 900 can be performed in anticipation of a gas update such as a gas refill or a gas injection. For example, a first gas update can be performed by adding a first gas mixture from the gas maintenance system 120 to the chamber 110, and after some period of time of use of the chamber 110, the procedure 900 can be performed. After the procedure 900 is performed, then a second gas update can be performed by adding an adjusted second gas mixture to the chamber 110 from the gas maintenance system 120. The adjusted second gas mixture has a concentration of fluorine (or an amount of fluorine) that can be based on the measurement made by the procedure 900.

The fluorine can be chemically reacted with the metal oxide 145 (910) by forming an inorganic fluoride compound plus oxygen. This inorganic fluoride compound (which is present in the new gas mixture 155) does not interact with the sensor 115.

After the fluorine is chemically reacted with the metal oxide 145 to form the new gas mixture 155 (910), the new gas mixture 155 can be transferred from the reaction vessel 135 into the measurement vessel 170, to enable the concentration of oxygen in the new gas mixture 155 to be sensed (915). The concentration of the oxygen in the new gas mixture 155 can therefore be sensed (915) by exposing the sensor 115 within the measurement vessel 170 to the new gas mixture 155. The concentration of oxygen in the new gas mixture 155 is sensed (915) without having to dilute the mixed gas 150 with another material.

Moreover, it may be appropriate to wait to sense the concentration of oxygen in the new gas mixture 155 (915) until or only after a pre-determined period of time has elapsed after the beginning of the chemical reaction (910). This would ensure that enough of the fluorine in the mixed gas 150 has been converted into oxygen and the inorganic fluoride compound before exposing the sensor 115 to the new gas mixture 155. The sensor 115 is therefore insulated from being exposed to the fluorine, which could cause damage to the sensor 115. It can take several seconds or minutes, depending on the relative amount of fluorine in the mixed gas 150 and the total volume of the metal oxide 145, to fully convert the fluorine into oxygen.

In some implementations, it is possible that the chemical reaction (910) can be implemented by flowing the mixed gas 150 at a low rate (for example, about 0.1 slpm or less) over or through the metal oxide 145 to form the new gas mixture 155 at a specific flow rate. In this case, the oxygen can be sensed (915) in a continuous fashion. The concentration of fluorine can be estimated (920) from either the integration of the sensed oxygen measurement (915) over a period of time, or when the sensed oxygen measurement (915) has reached a steady state.

The fluorine in the new gas mixture 155 is estimated (920) based on the sensed concentration of oxygen (915) and also based on the knowledge of the chemical reaction that converts the fluorine in the mixed gas 150 into the oxygen.

Upon completion of the procedure 900 (that is, after the concentration of fluorine within the mixed gas 150 has been estimated at 920), then the new gas mixture 155 is exhausted (removed) from the measurement vessel 170 to permit the procedure 900 to be performed again on a new batch of mixed gas 150.

Figure 10:
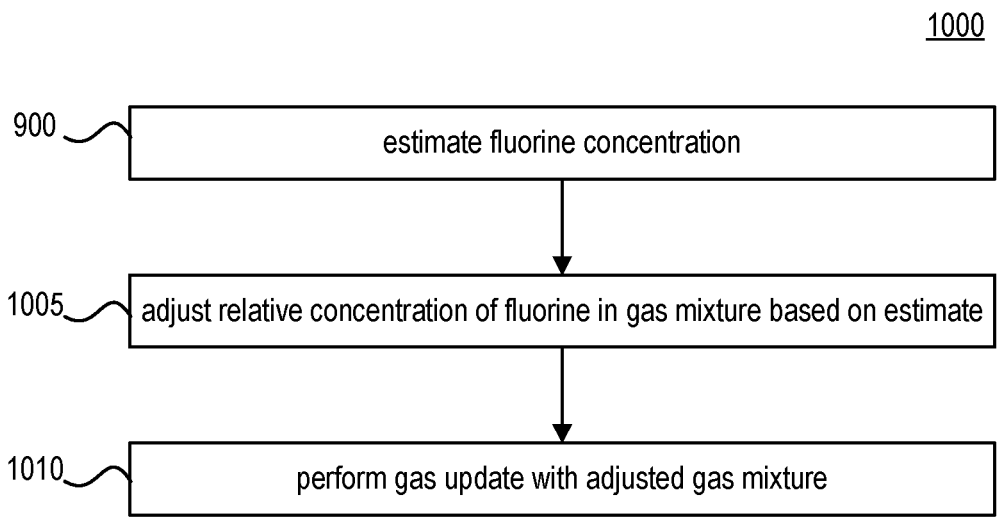
FIG. 10 is a flow chart of a procedure performed by the apparatus once the fluorine concentration is estimated and upon completion of the procedure of FIG. 9.

Referring to FIG. 10, a procedure 1000 is performed by the apparatus 100 once the fluorine concentration is estimated (920) and upon completion of the procedure 900. The gas maintenance system 120 receives the output from the controller 130 of the detection apparatus 105 and adjusts a relative concentration of fluorine in a gas mixture from a set of gas supplies (such as gas sources 651A, 651B, 651C, etc.) based on the estimated concentration of fluorine (1005). The gas maintenance system 120 performs a gas update by adding the adjusted gas mixture to the chamber 110 via the conduit system 127 (1010) until the pressure within the chamber 110 reaches a required level. The gas update can be completed and tracked by monitoring the timing of the valves within the gas maintenance system 120.

For example, with reference to FIG. 2, the gas update (1010) can include filling the gas discharge chamber 210 with a mixture of a gain medium and a buffer gas as well as fluorine, where the gain medium includes a noble gas and the fluorine and the buffer gas includes an inert gas. It is possible to delay the performance of the gas update (1010) relative to when the fluorine concentration estimation (900) is performed. In some implementations, the adjustment (1005) and the gas update (1010) can be performed immediately after the estimation (900) if the controller 130 determines that the concentration of fluorine in the gas mixture 107 has fallen below an acceptable level. In some implementations, it is possible to delay the adjustment of the fluorine (1005) until it is determined that the concentration of fluorine in the gas mixture 107 has fallen below an acceptable level. For example, if the controller 130 determines that the concentration of fluorine in the gas mixture 107 is still high, but the apparatus 100 must perform a gas update for other reasons, then, it is possible to perform the gas update without the goal of increasing the level of fluorine in the gas mixture 107.

Figure 11:
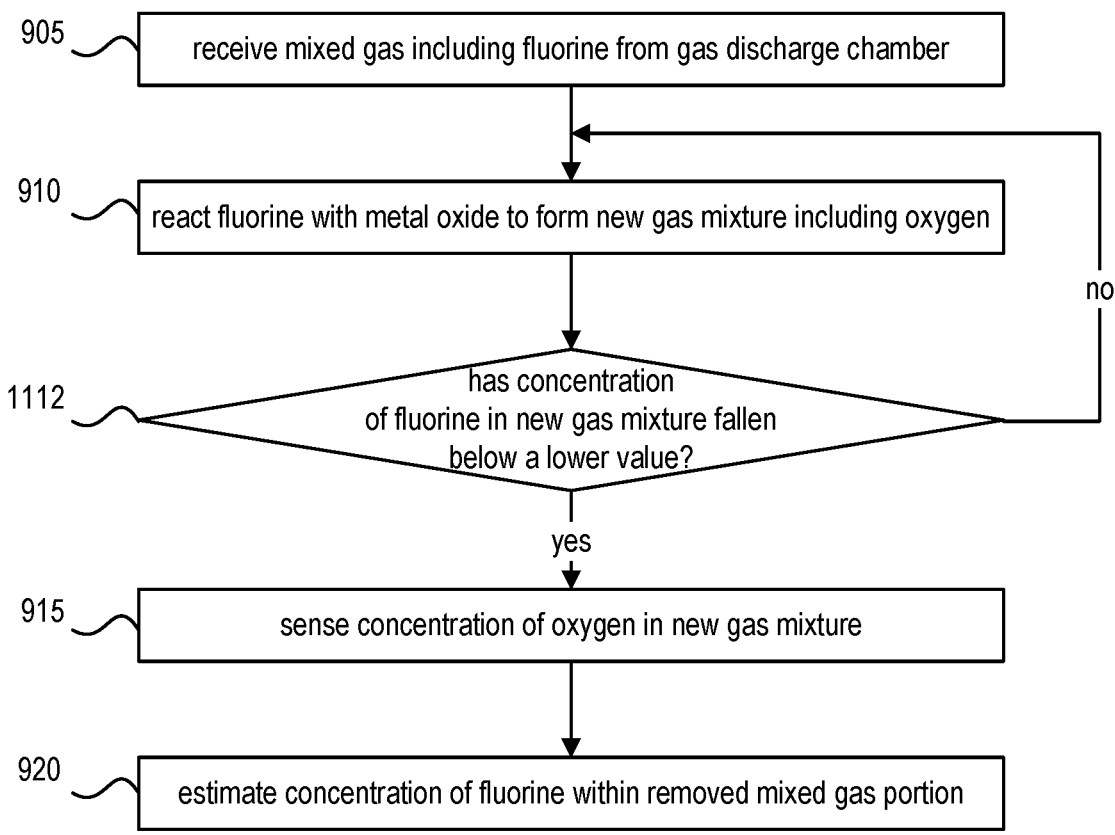
FIG. 11 is a flow chart of a procedure performed by the detection apparatus instead of the procedure of FIG. 9 to estimate the concentration of fluorine in the gas mixture in the chamber.

Referring to FIG. 11, in some implementations, the detection apparatus 305 performs a procedure 1100 instead of the procedure 900 to estimate the concentration of fluorine in the mixed gas 150. The procedure 1100 is similar to the procedure 900, including the steps of receiving the portion of the mixed gas 150 including fluorine from the gas discharge chamber 110 (905); and chemically reacting the fluorine in the mixed gas 150 with the metal oxide 145 to form the new gas mixture 155, which includes oxygen (910). The procedure 1100 determines whether the concentration of fluorine in the new gas mixture 155 falls below a lower value (1112). For example, the fluorine sensor 360 that is fluidly connected to the reaction cavity 140 can make this determination (1112) and the controller 330 can proceed forward with the step of sensing the concentration of oxygen in the new gas mixture 155 (915) only if the concentration of fluorine in the new gas mixture 155 has fallen below the lower value (1112). As before, the concentration of fluorine in the mixed gas 150 is estimated based on the sensed concentration of oxygen (920).

In some implementations, the lower value is a value determined based on the damage threshold of the sensor 115. In other implementations, the lower value is a value determined based on an error threshold of the sensor 115. For example, the lower value can be 0.1 ppm.

The embodiments may further be described using the following clauses:

1. A method comprising:
   receiving at least a portion of a mixed gas from a gas discharge chamber, wherein the mixed gas includes fluorine;
   reacting the fluorine in the mixed gas portion with a metal oxide to form a new gas mixture including oxygen;
   sensing a concentration of oxygen within the new gas mixture; and
   estimating a concentration of fluorine within the mixed gas portion based on the sensed concentration of oxygen.

2. The method of clause 1, wherein the metal oxide includes aluminum oxide.

3. The method of clause 1, wherein the metal oxide lacks an alkali metal, an alkaline earth metal, hydrogen, and carbon.

4. The method of clause 1, wherein the mixed gas is an excimer laser gas comprising at least a mixture of a gain medium and a buffer gas.

5. The method of clause 1, further comprising:
   adjusting a relative concentration of fluorine in a gas mixture from a set of gas supplies based on the estimated concentration of fluorine in the mixed gas portion; and
   performing a gas update by adding the adjusted gas mixture to the gas discharge chamber from the gas supplies.

6. The method of clause 5, wherein performing the gas update comprises filling the gas discharge chamber with a mixture of a gain medium and a buffer gas as well as fluorine.

7. The method of clause 6, wherein filling the gas discharge chamber with the mixture of the gain medium and the buffer gas comprises filling the gas discharge chamber with a gain medium that includes a noble gas and a halogen, and a buffer gas that includes an inert gas.

8. The method of clause 7, wherein the noble gas includes argon, krypton, or xenon; the halogen includes fluorine; and the inert gas includes helium or neon.

9. The method of clause 6, wherein filling the gas discharge chamber with the mixture of the gain medium and the buffer gas as well as fluorine comprises:
adding the mixture of the gain medium and the buffer gas as well as fluorine to an existing mixed gas in the gas discharge chamber; or
replacing an existing mixed gas in the gas discharge chamber with at least the mixture of the gain medium and the buffer gas as well as fluorine.

10. The method of clause 5, wherein performing the gas update comprises performing one or more of a gas refill scheme or a gas injection scheme.

11. The method of clause 1, further comprising:
determining whether the concentration of fluorine in the new gas mixture falls below a lower value;
wherein sensing the concentration of oxygen within the new gas mixture comprises sensing the concentration of oxygen within the new gas mixture only if it is determined that the concentration of fluorine in the new gas mixture has fallen below the lower value.

12. The method of clause 11, wherein the lower value is a value determined based on one or more of a damage threshold and an error threshold of a sensor that senses the concentration of oxygen within the new gas mixture.

13. The method of clause 11, wherein the lower value is 0.1 parts per million.

14. The method of clause 11, further comprising interacting the new gas mixture with an oxygen sensor to sense the concentration of oxygen only if it is determined that the concentration of fluorine in the new gas mixture has fallen below the lower value.

15. The method of clause 1, wherein receiving at least the portion of the mixed gas from the gas discharge chamber comprises receiving the mixed gas portion before a gas update is to be performed on the gas discharge chamber, wherein the gas update comprises adding a gas mixture to the gas discharge chamber from a set of gas supplies, wherein the gas mixture includes at least some fluorine.

16. The method of clause 15, wherein performing the gas update comprises performing one or more of a gas refill scheme or a gas injection scheme.

17. The method of clause 1, wherein receiving at least the portion of the mixed gas from the gas discharge chamber comprises bleeding the mixed gas from the gas discharge chamber and directing the bled mixed gas to a reaction vessel that houses the metal oxide.

18. The method of clause 17, further comprising transferring the new gas mixture from the reaction vessel to a measurement vessel, wherein the sensing the concentration of oxygen within the new gas mixture comprises sensing the concentration of oxygen within the new gas mixture within the measurement vessel.

19. The method of clause 17, wherein sensing the concentration of oxygen within the new gas mixture comprises exposing a sensor within the measurement vessel to the new gas mixture.

20. The method of clause 1, further comprising, after the concentration of fluorine within the mixed gas portion has been estimated, exhausting the new gas mixture from the measurement vessel.

21. The method of clause 1, wherein sensing the concentration of oxygen within the new gas mixture comprises sensing the concentration of oxygen within the new gas mixture without diluting the mixed gas portion with another material.

22. The method of clause 1, wherein reacting the mixed gas portion with the metal oxide to form the new gas mixture including oxygen comprises forming an inorganic fluoride compound plus oxygen.

23. The method of clause 22, wherein the metal oxide includes aluminum oxide, and the inorganic fluoride compound comprises aluminum fluoride.

24. The method of clause 23, wherein the total pore volume of the aluminum oxide is at least 0.35 cubic centimeters per gram.

25. The method of clause 1, wherein sensing the concentration of oxygen within the new gas mixture comprises sensing the concentration of oxygen within the new gas mixture only after a pre-determined period of time has elapsed after the beginning of the reaction.

26. The method of clause 1, wherein the mixed gas portion is an exhaust gas and reacting the mixed gas portion with the metal oxide to form the new gas mixture including oxygen comprises removing fluorine from the exhaust gas.

27. The method of clause 1, wherein estimating the concentration of fluorine within the mixed gas portion based on the sensed concentration of oxygen comprises estimating based only on the sensed concentration of oxygen and the chemical reaction between fluorine in the mixed gas portion and the metal oxide.

28. The method of clause 1, wherein the concentration of fluorine in the mixed gas portion is about 500-2000 parts per million.

29. The method of clause 1, wherein the reaction of the fluorine in the mixed gas portion with the metal oxide to form the new gas mixture including oxygen is stable.

30. The method of clause 1, wherein reacting the fluorine in the mixed gas portion with the metal oxide to form the new gas mixture including oxygen comprises performing a reaction that is linear and provides a direct correlation between the concentration of fluorine in the mixed gas portion and the concentration of the oxygen in the new gas mixture.

31. A method comprising:
performing a first gas update by adding a first gas mixture from a set of gas supplies to a gas discharge chamber;
removing at least a portion of a mixed gas from the gas discharge chamber after the first gas update, wherein the mixed gas includes fluorine;
reacting the fluorine of the removed mixed gas portion with a reactant to form a new gas mixture including oxygen;
sensing a concentration of oxygen within the new gas mixture;
estimating a concentration of fluorine within the removed mixed gas portion based on the sensed concentration of oxygen;
adjusting a relative concentration of fluorine in a second gas mixture from the set of gas supplies based on the estimated concentration of fluorine in the removed mixed gas portion; and
performing a second gas update by adding the adjusted second gas mixture to the gas discharge chamber from the gas supplies.

32. The method of clause 31, further comprising:
determining whether the concentration of fluorine in the new gas mixture falls below a lower value that is based on one or more of a damage threshold and an error threshold of a sensor that senses the concentration of oxygen within the new gas mixture; and wherein sensing the concentration of oxygen within the new gas mixture comprises sensing the concentration of oxygen within the new gas mixture only if it is determined that the concentration of fluorine in the new gas mixture has fallen below the lower value.

33. The method of clause 31, wherein the reactant comprises metal oxide.

34. The method of clause 31, wherein the mixed gas in the gas discharge chamber comprises an excimer laser gas including at least a mixture of a gain medium and a buffer gas.

35. The method of clause 31, wherein estimating the concentration of fluorine within the removed mixed gas portion based on the sensed concentration of oxygen comprises estimating the fluorine concentration within the removed mixed gas portion without measuring the fluorine concentration within the removed mixed gas portion.

36. An apparatus comprising a gas maintenance system comprising a gas supply system fluidly connected to one or more gas discharge chambers of an excimer gas discharge system;

a detection apparatus fluidly connected to each gas discharge chamber of the excimer gas discharge system, wherein the detection apparatus comprises:

a vessel defining a reaction cavity that houses a metal oxide and is fluidly connected to the gas discharge chamber for receiving mixed gas including fluorine from the gas discharge chamber in the reaction cavity, the vessel enabling a reaction between the fluorine of the received mixed gas and the metal oxide to form a new gas mixture including oxygen; and an oxygen sensor configured to be fluidly connected to the new gas mixture and, when fluidly connected to the new gas mixture, sense an amount of oxygen within the new gas mixture; and a control system connected to the gas maintenance system and the detection apparatus, and configured to:

receive the output of the oxygen sensor and estimate a concentration of fluorine in the mixed gas received from the gas discharge chamber;

determine whether a concentration of fluorine in a gas mixture from the gas supply system of the gas maintenance system should be adjusted based on the estimated concentration of fluorine in the mixed gas; and send a signal to the gas maintenance system to adjust the relative concentration of fluorine in a gas mixture supplied from the gas supply system of the gas maintenance system to the gas discharge chamber during a gas update to the gas discharge chamber.

37. The apparatus of clause 36, wherein each gas discharge chamber of the excimer gas discharge system houses an energy source and contains a gas mixture that includes an excimer laser gas including a gain medium and fluorine.

38. The apparatus of clause 36, wherein:

the detection apparatus also comprises a fluorine sensor fluidly connected to the reaction cavity and configured to determine whether a concentration of fluorine in the new gas mixture falls below a lower value, the lower value being a value determined based on one or more of a damage threshold and an error threshold of the oxygen sensor; and the control system is connected to the fluorine sensor, wherein the control system is configured to:

receive the determination from the fluorine sensor that the fluorine concentration in the new gas mixture falls below the lower value; and only permit the oxygen sensor to interact with the new gas mixture if it is determined that the concentration of fluorine in the new gas mixture falls below the lower value.

39. The apparatus of clause 36, wherein:

the detection apparatus further comprises a measurement vessel fluidly connected to the reaction cavity of the reaction vessel and defining a measurement cavity that is configured to receive the new gas mixture; and the oxygen sensor is configured to sense an amount of oxygen within the new gas mixture in the measurement cavity.

40. The apparatus of clause 36, wherein the oxygen sensor is configured to operate within an acceptable range only if the concentration of fluorine in the new gas mixture falls below a lower value.

41. The apparatus of clause 36, wherein the concentration of fluorine in the removed mixed gas portion is about 500-2000 parts per million.

42. The apparatus of clause 36, wherein the excimer gas discharge system includes a plurality of gas discharge chambers, and the detection apparatus is fluidly connected to each gas discharge chamber of the plurality, wherein the detection apparatus includes a plurality of vessels, each vessel defining a reaction cavity that houses the metal oxide, and each vessel being fluidly connected to one of the gas discharge chambers and the detection apparatus includes a plurality of oxygen sensors, each oxygen sensor associated with one vessel.

43. The apparatus of clause 36, wherein the excimer gas discharge system includes a plurality of gas discharge chambers, and the detection apparatus is fluidly connected to each gas discharge chamber of the plurality, wherein the detection apparatus includes a plurality of vessels, each vessel defining a reaction cavity that houses the metal oxide, and each vessel being fluidly connected to one of the gas discharge chambers and the detection apparatus includes a single oxygen sensor that is fluidly connected with all of the vessels.

Other implementations are within the scope of the following claims.

What is claimed is:

1. A method comprising:

receiving at least a portion of a mixed gas from a gas discharge chamber, wherein the mixed gas includes fluorine;

reacting the fluorine in the mixed gas portion with a metal oxide to form a new gas mixture including oxygen;

sensing a concentration of oxygen within the new gas mixture;

estimating a concentration of fluorine within the mixed gas portion based on the sensed concentration of oxygen; and determining whether the concentration of fluorine in the new gas mixture falls below a lower value;

wherein sensing the concentration of oxygen within the new gas mixture comprises sensing the concentration of oxygen within the new gas mixture only if it is determined that the concentration of fluorine in the new gas mixture has fallen below the lower value.

2. The method of claim 1, wherein the lower value is a value determined based on one or more of a damage threshold and an error threshold of a sensor that senses the concentration of oxygen within the new gas mixture.

3. The method of claim 1, further comprising interacting the new gas mixture with an oxygen sensor to sense the concentration of oxygen only if it is determined that the concentration of fluorine in the new gas mixture has fallen below the lower value.

4. An apparatus comprising
a gas maintenance system comprising a gas supply system fluidly connected to one or more gas discharge chambers of an excimer gas discharge system;
a detection apparatus fluidly connected to each gas discharge chamber of the excimer gas discharge system, wherein the detection apparatus comprises:
a reaction vessel defining a reaction cavity that houses a metal oxide and is fluidly connected to the gas discharge chamber for receiving mixed gas including fluorine from the gas discharge chamber in the reaction cavity, the reaction vessel enabling a reaction between the fluorine of the received mixed gas and the metal oxide to form a new gas mixture including oxygen;
an oxygen sensor configured to be fluidly connected to the new gas mixture and, when fluidly connected to the new gas mixture, sense an amount of oxygen within the new gas mixture; and
a fluorine sensor fluidly connected to the reaction cavity and configured to determine whether a concentration of fluorine in the new gas mixture falls below a lower value, the lower value being a value determined based on one or more of a damage threshold and an error threshold of the oxygen sensor; and
a control system connected to the gas maintenance system, the detection apparatus, and the fluorine sensor, and configured to:
receive the output of the oxygen sensor and estimate a concentration of fluorine in the mixed gas received from the gas discharge chamber;
determine whether a concentration of fluorine in a gas mixture from the gas supply system of the gas maintenance system should be adjusted based on the estimated concentration of fluorine in the mixed gas;
send a signal to the gas maintenance system to adjust the relative concentration of fluorine in a gas mixture supplied from the gas supply system of the gas maintenance system to the gas discharge chamber during a gas update to the gas discharge chamber;
receive the determination from the fluorine sensor that the fluorine concentration in the new gas mixture falls below the lower value; and
only permit the oxygen sensor to interact with the new gas mixture if it is determined that the concentration of fluorine in the new gas mixture falls below the lower value.

5. The apparatus of claim 4, wherein:
the detection apparatus further comprises a measurement vessel fluidly connected to the reaction cavity of the reaction vessel and defining a measurement cavity that is configured to receive the new gas mixture; and
the oxygen sensor is configured to sense an amount of oxygen within the new gas mixture in the measurement cavity.

6. The apparatus of claim 4, wherein the oxygen sensor is configured to operate within an acceptable range only if the concentration of fluorine in the new gas mixture falls below a lower value.

7. The apparatus of claim 4, wherein the concentration of fluorine in the removed mixed gas portion is about 500-2000 parts per million.

8. The apparatus of claim 4, wherein the excimer gas discharge system includes a plurality of gas discharge chambers, and the detection apparatus is fluidly connected to each gas discharge chamber of the plurality, wherein the detection apparatus includes a plurality of reaction vessels, each reaction vessel defining a reaction cavity that houses the metal oxide, and each reaction vessel being fluidly connected to one of the gas discharge chambers and the detection apparatus includes a plurality of oxygen sensors, each oxygen sensor associated with one reaction vessel.

9. An apparatus comprising
a detection apparatus fluidly connected to a gas discharge chamber, wherein the detection apparatus comprises:
a reaction vessel defining a reaction cavity that houses aluminum oxide and is fluidly connected to the gas discharge chamber for receiving mixed gas including fluorine from a gas mixture within the gas discharge chamber in the reaction cavity, the reaction vessel enabling a reaction between the fluorine of the received mixed gas and the aluminum oxide to form a new gas mixture including oxygen; and
an oxygen sensor configured to be fluidly connected to the new gas mixture and, when fluidly connected to the new gas mixture, sense an amount of oxygen within the new gas mixture; and
a control system connected to the detection apparatus and configured to estimate a concentration of fluorine in the mixed gas received from the gas discharge chamber based on the output of the oxygen sensor,
wherein the detection apparatus also comprises a buffer vessel between the gas discharge chamber and the reaction vessel, the buffer vessel configured to decouple a flow rate of an exhaust from the gas discharge chamber from a flow rate required for the reaction vessel.

10. The apparatus of claim 9, wherein the detection apparatus further comprises:
a measurement vessel fluidly connected to the reaction cavity and defining a measurement cavity that is configured to receive the new gas mixture; and
an oxygen sensor that is configured to sense the concentration of oxygen within the new gas mixture in the measurement cavity.

11. An apparatus comprising:
a detection apparatus fluidly connected to each gas discharge chamber of a light source that includes a plurality of gas discharge chambers, the detection apparatus comprising:
a plurality of reaction vessels, each reaction vessel defining a reaction cavity that houses a metal oxide, each reaction vessel being fluidly connected to one of the gas discharge chambers for receiving mixed gas including fluorine from the connected gas discharge chamber in the reaction cavity, the reaction vessel enabling a reaction between the fluorine in the received mixed gas and the metal oxide to form a new gas mixture including oxygen; and
a single oxygen sensor that is fluidly connected with all of the reaction vessels, the oxygen sensor configured to sense a concentration of oxygen within the new gas mixture formed in each reaction vessel; and
a control system configured to estimate a concentration of fluorine within the removed mixed gas portion of each gas discharge chamber based on the sensed concentration of oxygen within the new gas mixture formed in the reaction vessel for that removed mixed gas portion.

12. An apparatus comprising
a detection apparatus fluidly connected to each gas discharge chamber of an excimer gas discharge system, wherein the detection apparatus comprises:
  a reaction vessel defining a reaction cavity that houses a metal oxide and is fluidly connected to the gas discharge chamber for receiving mixed gas including fluorine from the gas discharge chamber in the reaction cavity, the reaction vessel enabling a reaction between the fluorine of the received mixed gas and the metal oxide to form a new gas mixture including oxygen;
  an oxygen sensor configured to sense an amount of oxygen within the new gas mixture; and
  a fluorine sensor fluidly connected to the reaction cavity and configured to determine whether a concentration of fluorine in the new gas mixture falls below a lower value, the lower value being a value determined based on one or more of a damage threshold and an error threshold of the oxygen sensor; and
a control system configured to:
  receive the output of the oxygen sensor and estimate a concentration of fluorine in the mixed gas received from the gas discharge chamber; and
  only permit the oxygen sensor to interact with the new gas mixture if the fluorine sensor determines that the concentration of fluorine in the new gas mixture falls below the lower value.

* * * * *